(12) United States Patent
Mosesov et al.

(10) Patent No.: US 12,349,968 B2
(45) Date of Patent: Jul. 8, 2025

(54) TISSUE ABLATION DEVICE WITH BROADBAND ANTENNA

(71) Applicant: Biocompatibles UK Limited, Camberley (GB)

(72) Inventors: Oleg Mosesov, Maple Grove, MN (US); Andrew Kevin Zachman, St. Michael, MN (US); Ankit Gajurel, Minneapolis, MN (US); Charles Senness, Hopkins, MN (US); Daniel T. Kollman, Andover, MN (US); Szymon Rzeszowski, Minneapolis, MN (US); Winston Tan, Plymouth, MN (US)

(73) Assignee: Biocompatibles UK Limited, Camberley (GB)

( * ) Notice: Subject to any disclaimer, the term of this patent is extended or adjusted under 35 U.S.C. 154(b) by 1118 days.

(21) Appl. No.: 16/980,833

(22) PCT Filed: Jan. 29, 2019

(86) PCT No.: PCT/IB2019/050716
§ 371 (c)(1),
(2) Date: Sep. 14, 2020

(87) PCT Pub. No.: WO2019/150258
PCT Pub. Date: Aug. 8, 2019

(65) Prior Publication Data
US 2021/0153936 A1    May 27, 2021

Related U.S. Application Data

(60) Provisional application No. 62/625,433, filed on Feb. 2, 2018.

(51) Int. Cl.
*A61B 18/18* (2006.01)
*A61B 18/00* (2006.01)

(52) U.S. Cl.
CPC .............. *A61B 18/1815* (2013.01); *A61B 2018/00023* (2013.01); *A61B 2018/00577* (2013.01);
(Continued)

(58) Field of Classification Search
CPC .............. A61B 18/1815; A61B 2018/1884
See application file for complete search history.

(56) References Cited

U.S. PATENT DOCUMENTS 5,370,677 A * 12/1994 Rudie ............... A61N 5/045
606/41
5,741,249 A    4/1998 Moss et al.
(Continued)

FOREIGN PATENT DOCUMENTS

CN    112004492    10/2024
WO    2019/150258 A2    8/2019

OTHER PUBLICATIONS

International Preliminary Report on Patentability received for PCT Patent Application No. PCT/IB2019/050716, mailed on Aug. 13, 2020, 8 pages.
International Search Report and Written Opinion received for PCT Patent Application No. PCT/IB2019/050716, mailed on Sep. 20, 2019, 12 pages.
(Continued)

*Primary Examiner* — Ronald Hupczey, Jr.
(74) *Attorney, Agent, or Firm* — Pauly, DeVries Smith & Deffner LLC

(57) ABSTRACT

The present invention provides a microwave ablation probe comprising an antenna including a helical arm and a linear arm.

20 Claims, 12 Drawing Sheets

(52) U.S. Cl.
CPC ................. *A61B 2018/1846* (2013.01); *A61B 2018/1869* (2013.01)

(56) References Cited

U.S. PATENT DOCUMENTS

| | | | |
|---|---|---|---|
| 6,223,085 B1 | 4/2001 | Dann et al. | |
| 2004/0133254 A1* | 7/2004 | Sterzer | A61B 18/18 607/101 |
| 2005/0245920 A1* | 11/2005 | Vitullo | A61B 18/18 607/156 |
| 2011/0066144 A1 | 3/2011 | Bonn et al. | |
| 2013/0165915 A1* | 6/2013 | Thiel | A61B 18/14 606/41 |
| 2015/0119870 A1* | 4/2015 | Rudie | A61B 18/1815 606/33 |
| 2015/0366612 A1 | 12/2015 | Crump et al. | |
| 2015/0366613 A1 | 12/2015 | Crump et al. | |

OTHER PUBLICATIONS

"First Examination Report," for Australian Patent Application No. 2022201194 mailed May 24, 2023 (4 pages).

"Response to First Examination Report," for Australian Patent Application No. 2022201194 filed Feb. 21, 2024 (16 pages).

"Second Office Action," for Chinese Patent Application No. 201980023159.6 mailed Apr. 29, 2024 (10 pages) with English Summary.

"Communication Pursuant to Article 94(3) EPC," for European Patent Application No. 21188416.8 mailed Jul. 8, 2024 (4 pages).

"Response to Second Office Action," for Chinese Patent Application No. 201980023159.6 filed Jun. 24, 2024 (9 pages) no English translation.

"Response to Communication Pursuant to Article 94(3) EPC," for European Patent Application No. 21188416.8 filed Nov. 5, 2024 (23 pages).

* cited by examiner

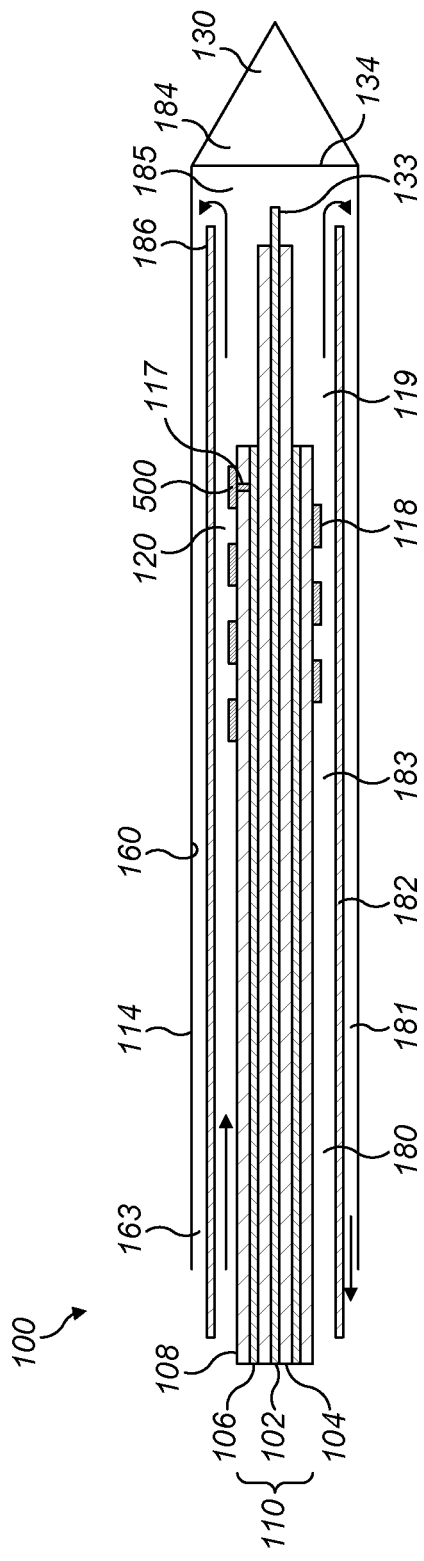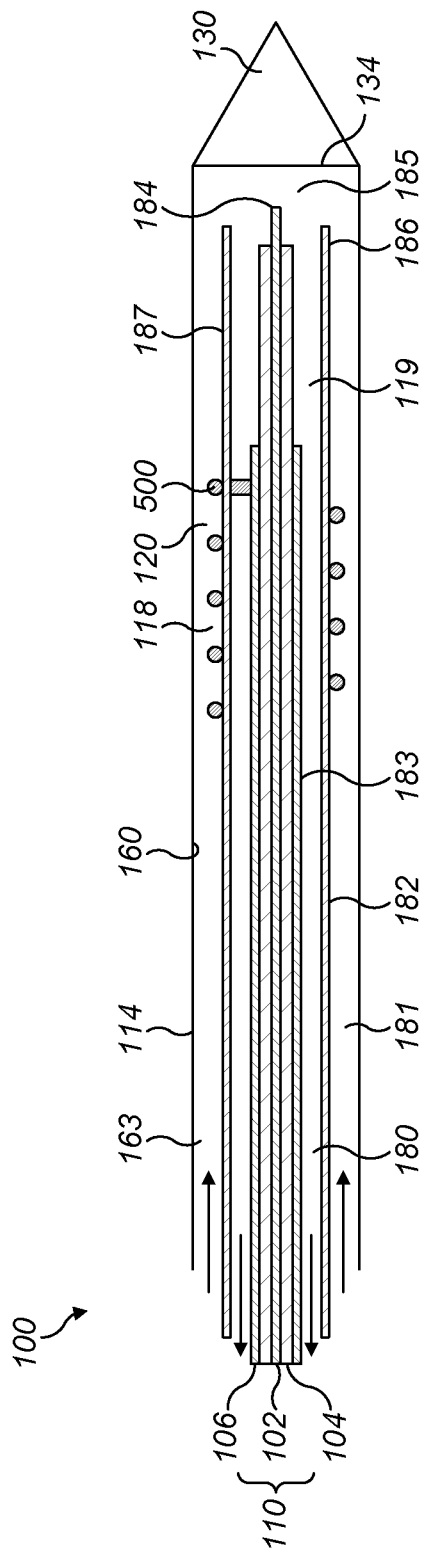

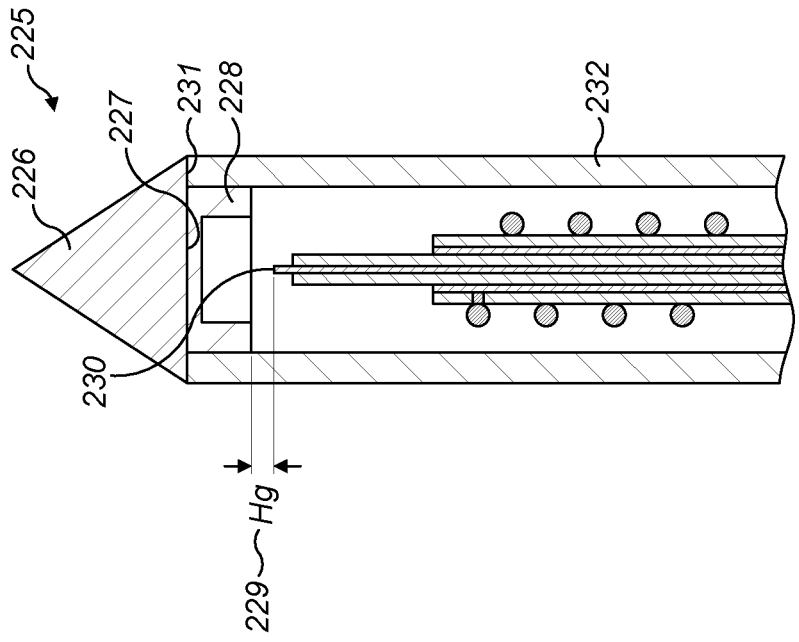
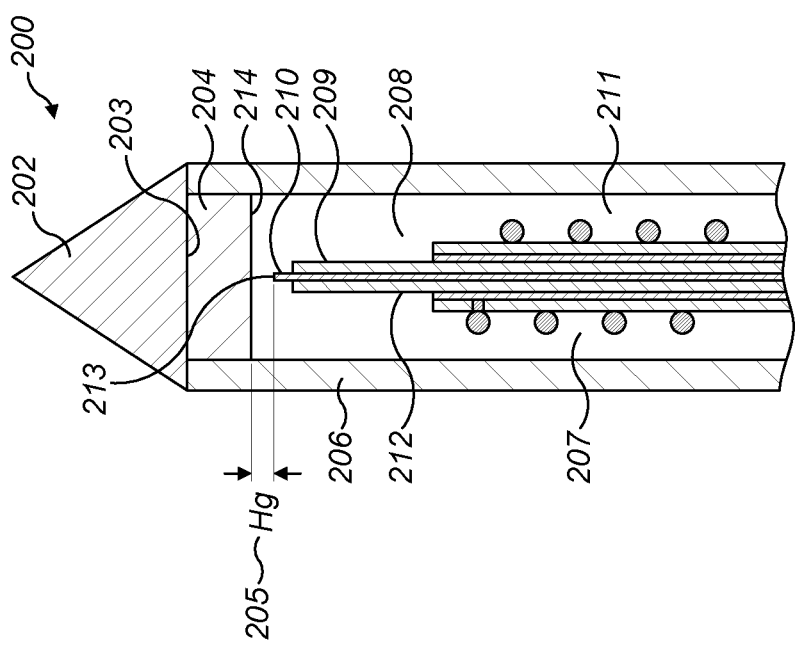

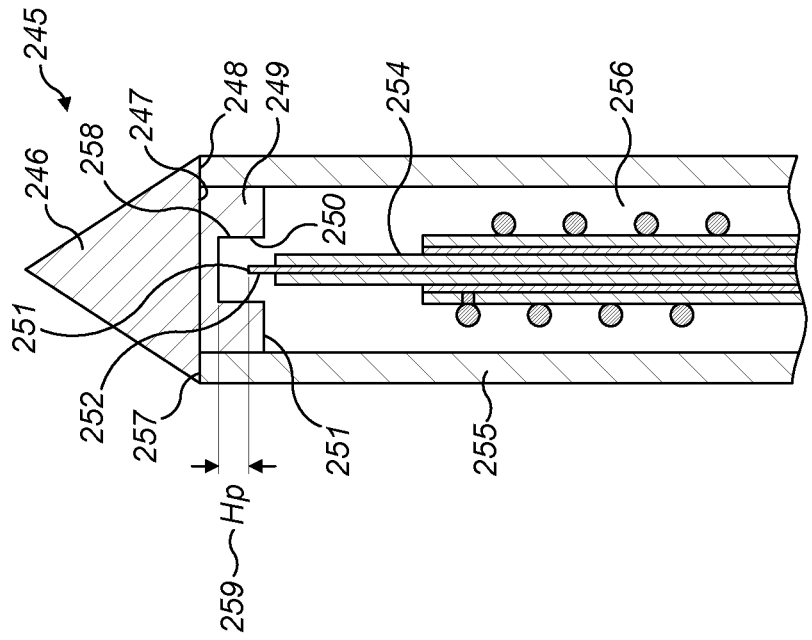
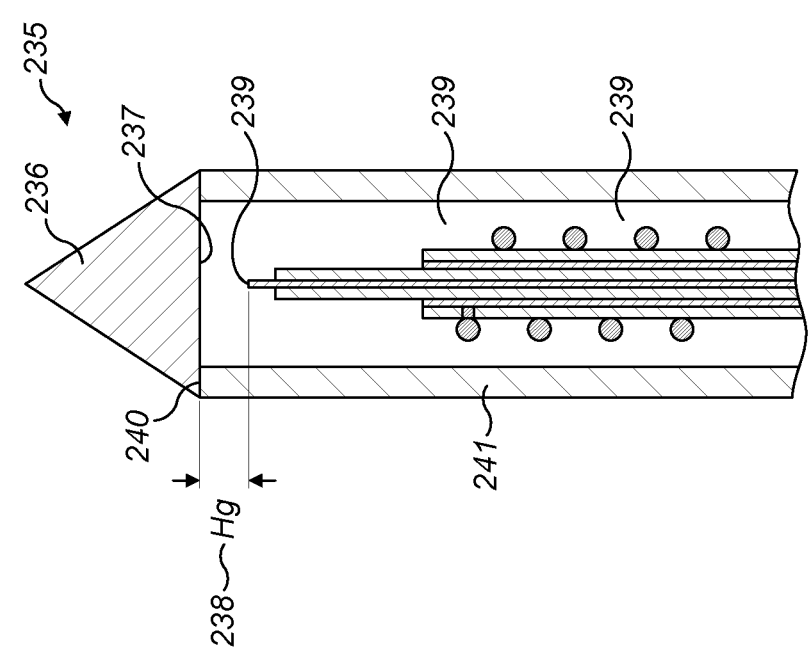

TISSUE ABLATION DEVICE WITH BROADBAND ANTENNA

CROSS-REFERENCE TO RELATED APPLICATION

This application is a U.S. 371 Application of International Application PCT/IB2019/050716, filed Jan. 29, 2019, which claims priority to U.S. patent application 62/625,433, filed Feb. 2, 2018, all of which are herein incorporated by reference in their entireties.

FIELD OF INVENTION

The present invention generally relates to tissue ablation devices and methods of use.

BACKGROUND OF THE INVENTION

In the treatment of diseases such as cancer, certain types of tissues have been found to denature at elevated temperatures. These types of treatments, known generally as hyperthermia therapies, typically utilize electromagnetic radiation to heat cancerous tissue to temperatures above 60° C. while maintaining healthy tissue at lower temperatures where irreversible cell destruction will not occur. Microwave ablation is one of such treatments utilizing electromagnetic radiation to heat tissue.

Microwave tissue ablation is a less invasive procedure than surgical removal and is preferred in many situations when tumors are difficult to remove by surgery, for example when the tumor is relatively small, disposed close to a relatively small organ, or disposed close to a major blood vessel. The approach has been used in organs such as the prostate, heart, and liver, where surgical removal of tumors may be difficult to perform.

In order to effectively plan and optimize the procedure, it is desired that the ablation device causes predictably sized and shaped volumes of ablation. For this reason regularly shaped, predictable ablation volumes are preferred, and it is particularly preferred to produce spherical, or near spherical ablation volumes. An ablation device with predictably sized and shaped ablation volumes simplifies the surgical procedures and reduces the undesirable medical complications.

One issue associated with microwave tissue ablation devices relates to the shape of the energy emission field, which would normally be of a teardrop shape with the larger head shape disposed in a distal direction of the device and an elongated tail, or cone shape disposed in a proximal direction. The ablation device is typically positioned such that the head shape is applied to the target tissue. The elongated cone is typically undesirable, because it leads to damage to non-targeted tissue along the insertion track.

Another issue associated with microwave ablation devices is that they have to operate within prescribed frequency ranges that are both suitable for dielectric heating and available as regulated for medical use. Suitable frequency bands exist in the 915 MHz range (902 to 928 MHz) the 2.45 GHz range (2.402 to 2.483 GHz) and in the 5.8 GHz range (5.725 to 5.875 GHz), although typically the 2.45 GHz range is preferred. It is desired for the antenna should match the tissue impedance so that the maximum peak of energy absorption by the target tissue falls at or about the frequency at which the antenna operates. However, as the procedure progresses, the tissue become denatured and the tissue impedance changes. In some situations, these tissue impedance changes cause the absorption peak to shift away from the desired frequency. This makes the tissue ablation less effective. In addition, the microwave energy that is not absorbed, may be reflected. The reflected microwave energy may cause the device itself to overheat prematurely which increases the possibility of device failure.

The embodiments disclosed herein are directed to reduce the effect of the above mentioned issues associated with microwave tissue ablation devices. More specifically, the embodiments disclosed herein provide microwave antennas and ablation devices that are able to operate across a broad frequency band and so can operate in more than one permitted spectrum. They create a microwave emission field closer to an ideal globular shape, and/or improve the tissue impedance match so that the energy absorption peak can be more closely maintained at or about the applied frequency during the tissue ablation process.

SUMMARY OF THE INVENTION

The present invention particularly provides tissue ablation devices and methods of use. More specifically, the present invention relates to a tissue ablation device that has an asymmetric dipole antenna.

A first aspect of the present invention provides a tissue ablation device including an asymmetrical dipole antenna comprising a feedline having an inner conductor, an outer conductor and a dielectric disposed there-between; an asymmetric dipole antenna comprising a helical arm electrically connected to the outer conductor of the feedline at a junction point, the helical arm extending proximally in a series of turns about the feedline, the proximal end of the helical arm being electrically floating; and a linear arm extending distally from the end of the feedline and electrically connected to the inner conductor, the linear arm comprising two portions, a first portion surrounded by a dielectric, and a second portion distal to the first portion which is exposed, that is to say it lacks said dielectric.

In one aspect, the tissue ablation devices herein include a microwave tissue ablation device having a metal cap disposed at a distal end of the tissue ablation device. In one embodiment, the metal cap includes a hollow-cylinder protrusion, wherein a proximal portion of the hollow-cylinder protrusion axially overlaps with a distal portion of an asymmetric dipole antenna. Alternatively, the metal cap includes a hollow-cylinder protrusion, wherein there is a gap axially disposed between a proximal end of the hollow-cylinder protrusion and a distal end of the helical antenna. Alternatively, the metal cap includes a solid-cylinder protrusion, wherein there is a gap axially disposed between a proximal end of the solid-cylinder protrusion and a distal end of the helical antenna.

In one preferred arrangement, the metal cap is configured to be electromagnetically coupled to the antenna via the linear arm. Preferably it is not physically coupled to the linear arm of the antenna. The closer the distal end of the linear arm of the antenna is to metal cap, the more the metal cap is electromagnetically coupled as part of the antenna.

Most conveniently, the tissue ablation device is a microwave ablation probe comprising a feedline the feedline being typically co-axial having an inner conductor, a dielectric coaxially disposed about the inner conductor and an outer conductor coaxially disposed about the dielectric. The feedline may comprise a dielectric or insulator layer coaxially disposed about the outer conductor. The device comprises an antenna, the antenna including, a helical arm, the helical arm being electrically connected to the outer conductor of the feedline at a junction point, the helical arm coaxially disposed about the feedline and extending in a proximal direction from the junction point. The antenna additionally comprises a linear arm, the linear arm being electrically connected to the inner conductor of the feedline, the linear arm extending in a distal direction from a distal end of the feedline, the linear arm further including a first portion surrounded by a dielectric, and a second portion free of dielectric, the second portion being distal to the first portion.

A still more preferred device comprises a microwave ablation probe, preferably a needle. The microwave ablation probe comprises a feedline electrically connected to a microwave antenna. The microwave antenna is preferably configured to emit microwave radiation in a frequency band selected from the 915 MHz band (902 to 928 MHz) the 2.45 GHz band (2.402 to 2.483 GHz) and/or the 5.8 GHz band (5.725 to 5.875 GHz). The microwave ablation probe having a probe shaft comprising a distal cap that is preferably configured for penetration of tissue. The needle shaft surrounds and is preferably co-axial with, the microwave antenna and at least a distal portion of the feedline. The needle shaft comprises a metallic portion and a non metallic portion, the non metallic portion extending axially to be co-extensive with at least the radiating portion of the antenna. The non metallic portion extends axially and circumferentially such that the shaft is preferably non metallic between the proximal and distal extent of the non metallic portion. The arrangement is useful for the antennas described further herein.

The non metallic portion may extend distally beyond the distal most portion of the antenna, and preferably extends distally to the cap. The non metallic portion may extend proximally to a point between the hub and the proximal most point of the antenna, but does not, in this embodiment, extend to the hub.

Where the microwave ablation device has a shaft comprising a metallic portion and a non metallic portion, the shaft may additionally comprise a resilient element between the metallic portion and the non metallic portion, configured to provide resilience to the joint. This reduces strain on the joint in use, for example during insertion of an ablation needle. Preferably the tissue ablation device further comprises a cooling system configured to cool the antenna and/or the feed line. The cooling system may be configured to cool the antenna and at least the distal most portion of the feedline by passing a coolant fluid over this portion of the feedline and the antenna.

Other embodiments of the invention are discussed throughout this application. Any embodiment discussed with respect to one aspect of the invention applies to other aspects of the invention as well, and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention. The following includes definitions of various terms and phrases used throughout this specification.

The term "spherical shape" means a three dimensional shape that is generally globular.

The term "distal" refers to a position or portion that is furthest from the user and the term "proximal" refers to a position or portion that is closest to the user.

The term "pitch" of a helical antenna is the height of one complete helix turn, measured parallel to the axis of the helix.

The terms "electrically connected," "electrically coupled," or "in electrical contact" are defined as electric current being able to pass from one item to the other. Typically the two items are physically connected by or through a conductor, e.g., a metal wire.

The term "electro-magnetically coupled" is defined as electro-magnetic energy being able pass from one item to the other without a physical contact such as to effect the shape of the energy field and the ablation volume produced. The two items need not be physically connected by or through a conductor, but the electro-magnetic energy can be transferred from one item to the other, e.g., electro-magnetic induction.

The terms "insulating layer," "dielectric," and "insulator," mean a layer of non-conducting material that does not form any electrical contact under operable use of the device. In the embodiments disclosed herein, the insulating layer or dielectric layer are used to prevent undesired electrical contact.

The terms "about" and "approximately" are defined as being close to as understood by one of ordinary skill in the art, and in non-limiting embodiments the terms are defined to be within 20%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The assemblies, devices or methods disclosed herein can "comprise," "consist essentially of," or "consist of" particular method steps, ingredients, components, compositions, etc.

Other objects, features and advantages disclosed herein will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

Advantages of the present invention may become apparent to those skilled in the art with the benefit of the following detailed description and upon reference to the accompanying drawings.

FIG. 1C is a simplified sectional view of a microwave tissue ablation device having a further alternative cooling system according to one embodiment of the disclosure.

FIG. 1D is a simplified sectional view of a microwave tissue ablation device having a further alternative cooling system according to one embodiment of the disclosure.

FIG. 2A is a schematic view of a microwave tissue ablation device with a metal cap according to one embodiment of the invention.

FIG. 2B is a schematic view of a microwave tissue ablation device with a metal cap according to one embodiment of the invention.

FIG. 2C is a schematic view of a microwave tissue ablation device with a metal cap according to one embodiment of the invention.

FIG. 2D is a schematic view of a microwave tissue ablation device with a metal cap according to one embodiment of the invention.

Figure 1:
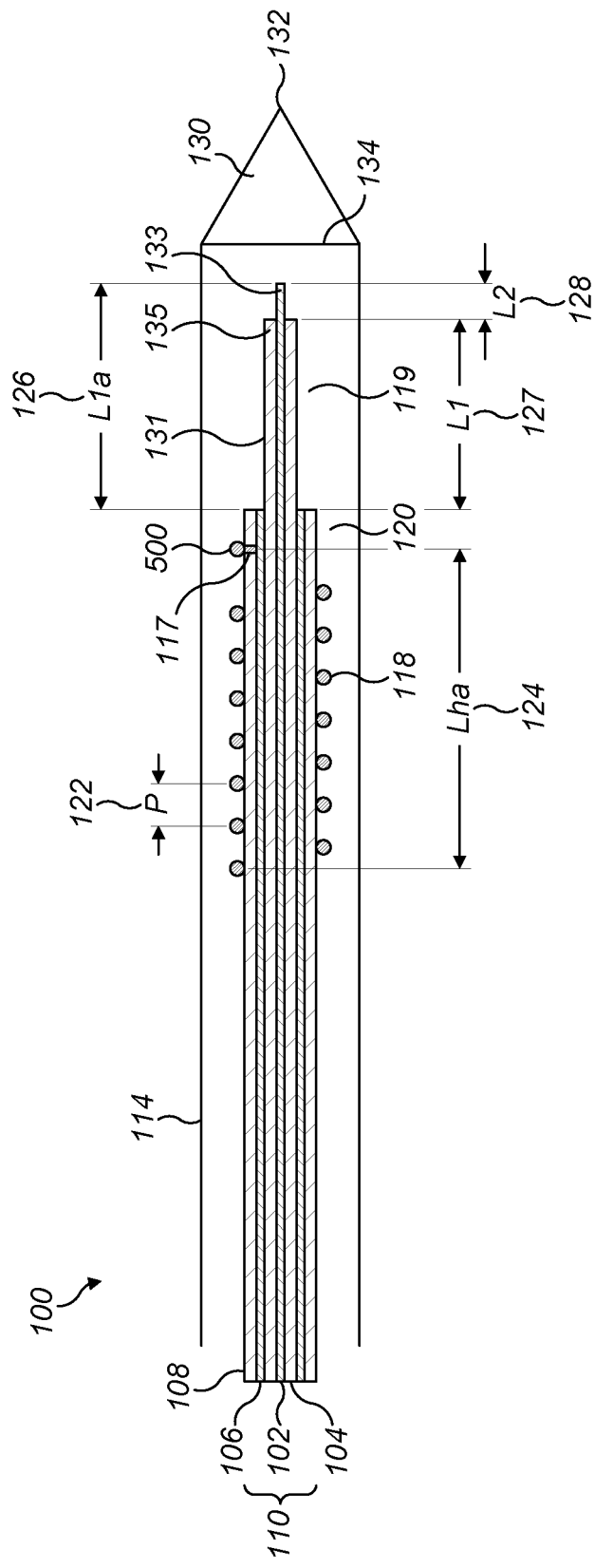
FIG. 1 is a simplified sectional view of a microwave tissue ablation device according to one embodiment of the disclosure.

While the invention is susceptible to various modifications and alternative forms, specific embodiments thereof are shown by way of example in the drawings. The drawings may not be to scale.

DETAILED DESCRIPTION OF THE INVENTION

The size and dimension of the ablation area created by the microwave tissue ablation device is dependent, among other factors, on the type of microwave antenna. Clinicians may select a microwave antenna capable of generating an ablation region greater than the size and dimension of the target tissue and insert the microwave antenna such that the ablation region created by the microwave antenna includes the target tissue. Where the tissue to be ablated is larger than the size of the ablation volume produced by the device, more than one device may be used and the ablation volumes combined to cover the tissue to be ablated. The embodiments of the microwave tissue ablation device described herein may be used to create predictably shaped ablation regions, with reduced tailing which aids ablation planning and prevents damage to tissue outside the volume to be treated.

The ablation devices disclosed herein are microwave ablation devices; that is to say they cause ablation by emission of microwave energy, which kills the tissue by heating. Typically the devices are microwave ablation needles having microwave antennas such as those described herein. The microwave energy may be generated by a microwave generator and supplied to the antenna by a power line which electrically connects the microwave generator to the feedline of the antenna within the needle. The microwave ablation devices also have a shaft surrounding and typically co-axial with both the microwave antenna and at least a distal portion of the feedline. The shaft typically extends from a proximal hub to a distal cap.

The microwave antenna is configured to emit microwave radiation in a frequency band selected from the 915 MHz band (902 to 928 MHz) the 2.45 GHz band (2.402 to 2.483 GHz) and/or the 5.8 GHz band (5.725 to 5.875 GHz). The preferred wavelength is within the 2.45 GHz band and particularly the antenna is preferred to be configured to emit microwave energy at or about 2.45 GHz. The devices are configured to operate at up to 150 watts power supplied to the antenna.

The feedline preferably comprises an inner conductor, an outer conductor and a dielectric disposed there-between. The feedline may comprise a further dielectric or insulator which insulates the outer conductor from other parts of the device and acts as an outer insulator to the feedline, but it is not required in all embodiments. In some embodiments the further dielectric may be absent from the distal portion of the feedline, at least up to the junction point. The feedline may lack such a further dielectric within the device shaft, such as between a proximal feedline connector of a distal hub, and the junction point of the antenna. The feedline is typically a co-axial cable having a central conductor, surrounded by a first dielectric, or insulator, the first dielectric being surrounded by the second conductor, which may be covered, by the further dielectric or insulator as described above. The inner conductor is typically the power conductor.

The devices of the present invention may comprise an asymmetric dipole antenna. This antenna preferably comprises two arms, a helical arm and a linear arm as described further herein. The distal end of the helical arm forms an electrical connection with the outer conductor of the feedline at a junction point. The junction point is conveniently towards, or at, the distal most end of the feedline. The feedline may extend beyond the junction point in order to provide suitable mechanical support to the electrical junction, but preferably it not extend by more than 5 mm and particularly not more than 1 mm beyond the junction point.

The helical arm extends proximally from the junction point in a series of turns about the feedline and so is coaxially disposed about the feedline. The helical arm preferably is not coiled in direct contact with the feedline. It may, for example form turns at a position radially displaced from the feedline. The helical arm is preferably coiled about a substrate that supports it. Where the feedline comprises an outer insulator, this outer insulator may be the substrate for the helical arm, which may form turns around the outer insulator. Alternatively the helical arm may, for example, be coiled about a tubular substrate, such as a cooling tube positioned about the feedline. Cooling tubes are described further below. The helical arm may be affixed to its substrate by an adhesive in order to hold it in place and to make assembly easier. The helical arm may be embedded within a matrix such as a polymer layer or coating in order to protect it, to insulate it from the other parts of the device, or to provide a seal as described further below.

Typically the helical arm is in the form of a single conductor. The helical arm of the antenna may be in the form of a wire or a ribbon, but is typically a wire having a circular cross section or a ribbon. The helical arm is preferably in the form of a cylindrical conductor, having a helical gap running from its proximal to its distal end to give a helical conductor having a planar conductor surface curved about the feedline. The helical arm does not make any other contact with either the inner conductor or the outer conductor, except at the junction point.

The linear arm of the antennas described herein is a conductor which is electrically connected to the inner conductor of the feedline and extends distally therefrom preferably on an axis co-axial with the helical arm and/or the feedline. The conductor is preferably in the form of a straight wire. In a particularly preferred embodiment, the linear arm includes a first, proximal, insulated portion and a second distal non insulated portion. Typically the first portion is surrounded by a dielectric and a second portion, distal of the first portion is free of dielectric. The second portion extends to the tip of the arm. The dielectric surrounding the first portion of the linear arm, preferably extends from the distal end of the feedline. In its simplest form, the linear arm of the antenna may be an extension of the feedline's inner conductor. The dielectric may then be an extension of the dielectric disposed between the central and outer conductors of the co-axial feedline.

Preferably the linear arm and the helical arm of the antenna are co-axial with the shaft of the ablation device, and thus the linear arm is co-axial with and extends distally from, the helical arm.

Preferably the overall length of the helical arm (Lha) can range from 1 to 18 mm, preferably the helical arm ranges from 4 to 10 mm. In an preferred embodiment, the helical arm ranges from 4 to 7 mm.

The total number of turns (N) is in the range of 1-12 but is not limited to integers. In preferred embodiments, N is typically from 4 to 8.

For each complete helical turn, the axial distance is a pitch (P), which can range from 0.7-1.5 mm, preferably, the pitch ranges from 1-1.5 mm and in a preferred embodiment, the pitch (P) of the helical arm is from 1.2-1.25 mm.

The number of helical loops (N), pitch (P) can affect the output of microwave energy, the shape of the emission field and the energy absorption spectrum. The judicious selection of each variable in combination can afford an ablation device with advantageous properties for tissue ablation.

The linear arm preferably has a length (Lla) of from 4 mm to 14 mm and preferably from 8 mm to 10 mm. The second, exposed portion preferably has a length (L2) of from 0.1 mm to 2 mm, preferably from 0.3 mm to 0.5 mm.

Thus in a preferred embodiment, the helical arm of the antenna is in the form of a ribbon, having a length (Lha) of 1 to 18 mm and comprises 1 to 14 turns, the linear arm of the antenna is 4 to 14 mm long and has a second, distal portion lacking dielectric of 0.1 to 3 mm mm long.

In a more preferred embodiment, the helical arm of the antenna is in the form of a ribbon, having a length (Lha) of 4 to 10 mm and comprises 4 to 8 turns, the linear arm of the antenna is 7 to 10 mm long and has a second, distal portion lacking dielectric of 0.3 to 0.5 mm mm long.

In a particularly preferred embodiment, the helical arm of the antenna is in the form of a ribbon, having a length (Lha) of 4 to 6 mm and comprises 3 to 5 turns. The linear arm is 7 to 10 mm long having a second, distal portion lacking dielectric 0.3 to 0.5 mm long.

Dimension descriptors are with reference to FIG. 1 purely for ease of reference.

The ablation device comprises a device shaft which preferably terminates distally in a device cap. The shaft is preferably cylindrical. The feedline and antenna are preferably disposed within the device shaft. The device shaft typically extends from a proximal hub and terminates distally in a distal cap. The diameter of the shaft is not limited, and is typically adapted for the intended purpose, for example for ablation needles, it is important to have a narrow needle to limit damage caused at insertion and to provide fine control of positioning, consequently the needle shaft is between 1.4 and 3 mm in diameter, preferably between 1.5 and 2.5 mm, particularly 2 to 2.5 mm.

The hub comprises electrical connections to electrical components of the shaft such as the feedline, and may also comprise cooling fluid inlet and outlet connections, where necessary.

The shaft is typically cylindrical and is typically made of a biocompatible polymer, a biocompatible composite material, such as glass fiber reinforced polymer or carbon fiber reinforced polymer, ceramic or metal (such as stainless steel). The shaft is preferably made of ceramic or metal, but in a preferred embodiment the shaft comprises metallic portion and a non metallic portion. The non metallic portion may be a biocompatible composite material, such as glass fiber reinforced polymer or carbon fiber reinforced polymer or ceramic, but is preferably ceramic due to its improved performance and strength. The ceramic is preferably an alumina or zirconia ceramic.

Where the shaft has a non metallic portion, the non metallic portion preferably extends axially to cover the antenna and thus is at least co extensive with the radiating portion of the antenna. In one embodiment the non metallic portion extends at least from the proximal most point of the helical arm to the distal end of the shaft. (i.e. the point of attachment of the tip of the device). The non metallic portion extends axially and circumferentially such that the shaft is preferably non metallic between the proximal and distal extent of the non metallic portion.

The shaft may further comprise an echogenic region on the outer surface configured to be visible under ultrasound, imaging. In one embodiment, this region comprises a coating comprising acoustically-reflective microspheres The echogenic region extends at least to cover the region of the shaft radially outward of the antenna. Where the shaft comprises a metallic portion and a non metallic portion, the joint between the two portions, where the metallic portion and the non metallic portion abut, maybe a point of potential weakness, especially where the non metallic portion is ceramic, since ceramic is typically less flexible and more brittle than metals such as stainless steel. It is therefore preferred the shaft additionally comprises a resilient element between this portion and the metallic portion configured to provide resilience to the joint between the non metallic portion and the metallic portion of the probe shaft in use. Although a resilient element may also be present between the non metallic region and the cap, it is not necessary since the strains on the shaft at this point are lower. The resilient element may, for example, comprise a resilient annular spacer, which may be made of a resilient thermoplastic elastomer, such as polyether block amide (PEBA)—tradename PEBAX® or Vestimid®E (Evonik Industries) or a polyaryletherketone (PAEK) such as Polyether ether ketone (PEEK). The spacer is preferably shaped and configured to space apart the proximal end of the non metallic portion from the distal end of the metallic portion. The resilient element preferably abuts the metallic portion on a proximal face and the non metallic portion on a distal face. The resilient annular spacer typically extends radially outward to form a surface flush with the outer surface of the probe shaft. The radially inner portion of the annular spacer may be extended proximally and/or distally to provide an annular step configured to support the inner face of the he proximal end of the non metallic portion and/or the distal end of the metallic portion. In one preferred embodiment, the annular spacer is extended proximally to provide an annular step configured to support the inner face of the distal end of the metallic portion, but does not extend distally. The device shaft may also comprise an adaptor sleeve to support the joint between the non metallic portion and the metallic portion of the shaft. The adaptor may be configured to take account of any differences in thickness between the non metallic portion and metallic portion of the shaft, such as to provide a smooth surface transition between the metallic and non metallic portions. It may be metallic, or non metallic such as a thermoplastic elastomer, such as a PEBA PEBAX® or Vestimid®E or a PAEK such as PEEK. The adaptor is particularly important where the non metallic portion is ceramic due to the thickness required for additional strength of the ceramic and the danger of flexing of the shaft causing cracking at this point. Conveniently the sleeve extends each side of the joint sufficiently to provide support for the joint and is typically positioned radially inward of the shaft, typically between the feedline and the inner wall of the shaft. The adapter sleeve is preferably metallic.

The resilient element and the adaptor sleeve together comprise a strain relief region. The resilient element and the adaptor sleeve may be a single piece or separate.

In one preferred embodiment, the strain relief region comprises a resilient element as described above, which comprises a resilient annular spacer shaped and configured to space apart the proximal end of the non metallic portion from the distal end of the metallic portion, the spacer configured to abut the metallic portion on a proximal face and the non metallic portion on a distal face, the spacer extending radially outward to form a surface flush with the outer surface of the probe shaft, the radially innermost portion of the spacer extending proximally to provide an annular step configured to support the inner face of the distal end of the metallic portion; the strain relief region additionally comprising an adaptor sleeve extending each side of the joint and radially inward of the annular spacer. Preferably the sleeve extends proximally of the annular spacer and is configured to be in contact with and support the inner face of the distal end of the metallic portion of the shaft; and preferably extends distally of the spacer and is configured to be in contact with and support the inner face of the proximal end of the ceramic portion of the shaft.

The ablation device preferably comprises a distal cap, which may be configured to seal the distal end of the device to prevent coolant fluid leakage or tissue fluid penetration. The cap may be manufactured as a separate part and may be configured to be attached to the shaft. The cap is preferably configured to aid insertion into tissues and to penetrate the skin of a patient and so may, for example, come to a distal point, or be configured as a trochar. The cap may be made of any suitable biocompatible material such as a biocompatible polymer, composite, ceramic or metal such as stainless steel. Where the cap is metal, the cap and the distal end of the antenna (i.e. the distal end of the linear arm of the antenna) may be configured, to be electromagnetically coupled. This can be done by adjusting the distance between the distal tip of the antenna and the cap so that they become electromagnetically coupled at the frequency and at the power at which the antenna is intended to operate. This effect can be used to tune the shape of the distal portion of the energy field generated by the antenna and hence the shape of the ablation zone. The cap and antenna need not, however be so coupled, i.e. the antenna may be electromagnetically decoupled from the cap. It is preferred that the tip and cap do not touch. In practice the gap between the tip and the cap is 0.2 mm or greater, particularly 0.2 mm to 3 mm and most preferably 1 to 2 mm. Most preferably is at or about 1.5 mm.

In one aspect, the portion of the linear arm lacking dielectric is partially or completely inserted into the metal cap, but does no touch the cap. This can be achieved by creating an open pocket in the base of the cap into which this part of the antenna or a portion of it is inserted. The degree to which the exposed distal tip is inserted influences the shape of the distal portion of the energy field and hence the shape of the ablation zone. The effect is illustrated in FIG. 7.

Where the distance between the tip and cap is greater than 3 mm they are not considered to be sufficiently coupled to be useful in shaping the ablation, particularly at 2.45 GHz.

Thus in a preferred embodiment, the helical arm of the antenna is in the form of a ribbon, having a length (Lha) of 1 to 18 mm and comprises 1 to 14 turns, the linear arm of the antenna is 4 to 14 mm long and has a second, distal portion lacking dielectric of 0.1 to 3 mm mm long, the portion lacking dielectric separated from the base of the cap by 0.2 to 3 mm.

in a more preferred embodiment, the helical arm of the antenna is in the form of a ribbon, having a length (Lha) of 4 to 10 mm and comprises 4 to 8 turns, the linear arm of the antenna is 7 to 10 mm long and has a second, distal portion lacking dielectric of 0.3 to 0.5 mm long the portion lacking dielectric separated from the base of the cap by 1 to 2 mm.

In a more preferred embodiment, the helical arm of the antenna is in the form of a ribbon, having a length (Lha) of 4 to 6 mm and comprises between 3 to 5 turns. The linear arm is 7 to 10 mm long having a second, distal portion lacking dielectric 0.3 to 0.5 mm long, the portion lacking dielectric separated from the base of the cap by 1 to 2 mm, preferably by at or about 1.5 mm.

The shape of the energy field and hence the ablation volume can also be influenced by the provision of a metallic sheath concentric with the feedline. The sheath is preferably cylindrical and extends over at least a portion of the feedline proximal to the antenna. The sheath may also extend over at least a portion of the antenna, but preferably it terminates at a point proximal to the distal most point of the helical arm of the antenna and does not extend over the antenna. Preferably the gap between the sheath and the distal most portion of the helical arm is at least 0.1 mm. The gap may be for example, between 0.1 to 2 mm or 0.1 to 1 mm, preferably it is at or about 0.5 mm. The sheath is preferably not placed on the outer surface of the shaft, but is preferably radially displaced from the feed line and co axial with it. Preferably it is placed between the feedline and the inner wall of the shaft. In one arrangement, the metal sheath may be the adaptor sleeve described above.

The ablation devices described herein are preferably configured to operate at powers of up to 150 watts and for periods of up to 20 minutes or more. The devices heat up during use due to resistive heating of the antenna and to energy reflected from the tissue and therefore typically at least the distal portion of the device including a distal portion of the feedline and the antenna will require cooling. Conveniently the whole feedline and antenna are cooled. Cooling the antenna prevents the device itself becoming damaged and prevents tissue close to the antenna becoming over heated or charred. This alters the physical properties of the tissue, including its energy absorption and reflection characteristics and therefore reduces the efficiency of the antenna and may alter the ablation zone. In an embodiment the tissue ablation devices above therefore may additionally comprise a cooling system to cool the antenna and/or at least a portion of the feed line. Such coolant systems are typically configured to pass a coolant such as a coolant fluid (e.g. water) over at least a portion of the feedline and over the antenna. Typically such systems comprise a coolant inlet and a coolant outlet which co-operate to pass a coolant over the antenna and optionally at least a portion of the feedline to cool the antenna and optionally at least a portion, preferably all, of the feedline. The antenna and feedline are typically in contact with the coolant.

In one option the coolant system comprises a coolant chamber surrounding the antenna and at least a distal portion of the feedline and having a coolant inlet conduit, configured to supply coolant to the coolant chamber and a coolant outlet conduit configured to carry coolant away from the coolant chamber, the coolant inlet and coolant outlet conduits configured to pass coolant over at least a portion of the feedline and at least a portion of the antenna.

Preferably the coolant chamber is defined between the inner walls of the device shaft. The chamber may be bounded distally by the cap and maybe bound proximally by one or more proximal seals, which close the cooling chamber proximally. The one or more seals are preferably formed at the hub or at a point between the hub and the proximal portion of the helical arm of the antenna. The cooling system comprises at least one coolant inlet conduit configured to deliver coolant fluid to the coolant chamber and at least one coolant outlet conduits to remove coolant fluid from the chamber. The coolant inlet and coolant outlet conduits typically pass through the proximal seal. In one approach, the coolant inlet conduit is a coolant inlet tube configured to deliver coolant to a position adjacent to and radially outward of the antenna and or feedline. In this case, the coolant inlet tube is preferably disposed within the coolant chamber between the antenna and the inner wall of the shaft. Preferably it is displaced radially outward of the feedline.

In an alternative arrangement the cooling system comprises a coolant inlet conduit and a coolant outlet conduit, each conduit arranged about at least a portion of the feedline and a portion of the antenna. Each conduit arranged in the form of a helix, the coolant inlet conduit and the coolant outlet conduit being interdigitated one with the other to form a double helix. In one preferred arrangement the cooling system comprises a pair of helical dividers arranged about the feedline and at least a part of the antenna in a double helix, each divider extending radially outward, towards the inner wall of the shaft and extending radially inward towards the antenna and/or the feedline such that the coolant inlet conduit and the coolant outlet conduit are formed between the two dividers and the coolant inlet conduit and coolant outlet conduit form a double helix. The dividers may be in the form of filaments or ribbons, or a combination of both. Where the dividers comprise a ribbon, the ribbon is preferably generally perpendicular to the inner shaft wall. The filaments may be formed of metal or of a resilient: polymer. The dividers preferably extend to seal against the inner wall and at least a portion of the antenna and/or feedline.

The cooling system may additionally comprise a coolant mixing chamber in fluid communication with both the coolant inlet and coolant outlet conduits, such that the coolant inlet and coolant outlet are in fluid communication via the coolant mixing chamber. The coolant mixing chamber is preferably configured to allow coolant to pass over at least a portion of the antenna, particularly at least a portion of the linear arm of the antenna. The coolant mixing chamber is particularly configured to allow coolant to pass over the distal portion of the linear arm of the antenna and at least a portion of the cap.

Alternatively and preferably, the cooling system comprises a coolant chamber defined between the inner walls of the device shaft. The chamber may be bounded distally by the cap and proximally by a seal between the hub and the shaft, or at some point distal from the hub and between the antenna and the hub as previously described. The coolant chamber surrounds the antenna and at least a distal portion of the feedline.

The cooling system further comprises a cooling tube disposed about the feedline, the cooling tube preferably extending distally about the feedline and preferably co-axial therewith. The cooling tube preferably divides the cooling chamber into a first cooling conduit and a second cooling conduit, the first cooling conduit disposed between the feedline and the inner wall of the cooling tube and the second cooling conduit disposed between the outer wall of the cooling tube and the inner wall of the device shaft. The cooling tube preferably extends over the distal portion of the feedline and extends distally about at least a portion of the antenna, preferably the cooling tube extends at least to the tip of the linear arm of the antenna. A variety of materials are suitable for the cooling tube, but it is preferably non metallic. Conveniently the cooling tube may be made of a thermoset polymer such as a polyimide or of a thermoplastic polymer resin such as polyethylene terephthalate (PET) or a fluropolymer such as polytetrafluroethylene (PTFE), or of a PAEK such as PEEK.

The helical arm of the antenna may be disposed within the first cooling conduit, for example the distal portion of the feedline may comprise a second insulator as described above, and the helical arm of the antenna is wound directly about the feedline, the second insulator extending axially at least between the helical arm and the second conductor of the feedline. in this case, the cooling tube may extend to cover a portion of the helical arm, but preferably to cover the helical arm and a portion of the linear arm, but most preferably the cooling tube extends at least to the distal end of the antenna, such that the first cooling conduit extends at least to the tip of the antenna.

Otherwise the cooling tube extends to cover the distal portion of the feedline and a portion of the linear arm, but most preferably the cooling tube extends at least to the distal end of the antenna, such that the first cooling conduit extends at least to the tip of the antenna.

The cooling system may additionally comprise a coolant mixing chamber in fluid communication with both the first coolant conduit and the second coolant conduit, such that the first coolant conduit and the second coolant are in fluid communication via the coolant mixing chamber. The coolant mixing chamber is preferably configured to allow coolant to contact a portion of the cap.

Either the first or the second cooling conduit may act as the coolant input conduit or coolant output conduit. The first and second coolant conduits are open at the distal end allowing the cooling fluid to circulate through the coolant mixing chamber between the distal end of the cooling tube and the base of the applicator cap.

The cooling tube preferably extends proximally towards the hub. The first cooling fluid conduit and second cooling fluid conduits are in fluid communication with cooling fluid input and output connectors of the hub, for the supply of cooling fluid and discharge of cooling fluid during use.

In a particularly preferred approach, the helical arm of the antenna, preferably in the form of a ribbon, is wound about the cooling tube. In this case, the helical arm is in electrical contact with the outer conductor of the feedline at the junction point and extends distally in a series of turns about the cooling tube as described above. In this case, the cooling tube preferably extends at least to the junction point of the antenna and feedline, preferably it extends, further, to cover at least a portion of the linear arm, but most preferably the cooling tube extends to the tip of the linear arm, such that the first cooling conduit extends at least to the tip of the antenna. Preferably the electrical contact between the distal end of the helical arm and the outer conductor of the feedline passes through the cooling tube.

In this approach it is preferred that the outer insulator does not extend over the distal portion of the feedline. Preferably it does not extend over at least the portion which extends from a point on the feedline immediately proximal of the helical arm of the antenna to the junction point. The outer insulator may be absent from the entire feedline within the shaft of the ablation device.

In embodiments in which the cooling system comprises a cooling tube as described above, the helical arm may be either a wire or a ribbon, but is most preferably a ribbon. The helical arm is preferably in the form of a cylindrical conductor, having a helical gap running from its proximal end to its distal end to give a helical conductor having a planar conductor surface disposed about the feedline and preferably co-axial with it.

The cooling systems described herein pass a coolant typically water over the feedline and at least a portion of the antenna, preferably the whole antenna. It is not necessary to insulate the antenna from the cooling fluid for normal operation. In some embodiments described herein parts of the feedline are lacking an outer insulator surrounding the feedline. The feedline may be lacking insulator between the hub and the junction point or its whole length within the device shaft. The helical arm of the antenna may also lack any insulation, particularly where it is wound about a coolant tube.

The ablation devices described herein may additionally comprise one or more temperature sensors, such as a thermocouples, to measure the temperature at points along the shaft. Typically a thermocouple may be located within the cooling system and configured to measure the temperature of the coolant or of other parts of the device such as the feedline or device shaft during operation of the device.

Ablation devices described herein typically comprise a proximal hub as discussed briefly above. The hub typically comprises connectors for connecting the feedline to an energy supply line, and for connecting electrical devices within the device shaft to control systems. Such connectors may be permanent or demountable. The hub may also comprise coolant manifold with input and output connectors for connecting the coolant input to a coolant supply and the coolant output to waste or recirculating system. The hub may also form part of a handle configured to provide a firmer grip for a surgeon to handle the tissue ablation device.

In a further aspect, the invention provides a system for microwave ablation of tissue comprising one or more microwave ablation devices such as probes or needles as described herein, the microwave ablation device comprising a microwave antenna configured to transmit microwave energy to tissue, a power module configured to provide microwave energy to the microwave antenna and one or more power cables configured to connect the power module to the microwave antenna of the ablation devices and to deliver microwave energy provided by the power module to the antenna for the ablation of tissue.

The power module is preferably configured to supply microwave energy to the antenna in one or more of the 915 MHz range the 2.45 GHz range or the 5.8 GHz range, preferably in the 2.45 GHz range and most preferably at or about 2.45 GHz. The power module may be configured to provide microwave energy to the antennas of up to 5 microwave ablation probes, preferably of one, two or three probes.

The system may also comprise a control module, configured to control the output of the power module. The control module may be configured to control one or more of the following parameters: the output wavelength, the output power, the time period over which microwave energy is delivered to one or more of the antennas, the time period over which energy is delivered at an output power. Where the ablation device comprises a temperature sensor the control module may be configured to control any one or more of the parameters in response to a signal from the temperature sensor. For example the control module may be configured to switch off the power to one or more of the antennas in response to an over temperature condition.

The power cable is preferably a coaxial cable which is preferably rated to at least 30 watts, preferably at least 100 watts, preferably at least 150 watts power. The cable may be a cooled cable configured to be cooled by a coolant supply, preferably by circulating coolant along the cable between a cable coolant inlet and a cable coolant outlet.

Particularly where the ablation device comprises a cooling system the system for microwave ablation may comprise a cooling system configured to deliver coolant to the cooling system of the microwave ablation device, to cool the device. This cooling system may comprise a coolant supply reservoir and a coolant line configured to deliver coolant to the ablation device to cool the device as described herein. The system preferably further comprises at least one pump configured to pump the coolant fluid from the coolant supply reservoir to the ablation device to cool the device. The system preferably also includes a coolant outlet line configured to carry coolant away from the ablation device. The coolant outlet line may deliver the coolant to waste or the system may comprise a coolant recirculation system and the coolant is delivered the coolant recirculation system. The coolant may be returned to the coolant reservoir for recirculation, for example.

The system for microwave ablation may comprise a cooling system configured to cool the electric cable. The system configured to cool the electric cable may comprise a coolant reservoir and a coolant line configured to deliver coolant to electric cable to cool the cable The system preferably further comprises at least one pump configured to pump the coolant fluid from the coolant supply reservoir to the cable to cool the cable. The system preferably also includes a coolant outlet line configured to carry coolant away from the cable The coolant outlet line may deliver the coolant to waste or the system may comprise a coolant recirculation system for cooling the electric cable and the coolant is delivered the coolant recirculation system. The coolant may be returned to the coolant reservoir for recirculation, for example.

In a further configuration the system comprises a cooling system and the cooling system is configured to cool both the cable and the microwave ablation device.

A further aspect of the invention is a method of using a microwave ablation device according to the invention.

The method includes a step preparing a console, wherein the console connects a microwave tissue ablation device with a power source and coolant source. In one embodiment, the console may support more than one microwave tissue ablation devices. For example, one console may support three or four tissue ablation devices providing sufficient electricity and coolant supply to each of the tissue ablation devices.

The method 1000 includes a step 1010 preparing the microwave tissue ablation device, wherein the microwave tissue ablation device includes an asymmetric dipole antenna. The microwave tissue ablation device in method 1000 can be the microwave tissue ablation devices shown in FIGS. 1-7.

The step 1010 may further include gathering other necessary supplies; obtaining room temperature sterile saline/water; obtaining an intravenous pole; placing the intravenous pole close to the surgery table; identifying target tissue location; determining a number of microwave tissue ablation device needed; obtaining the microwave tissue ablation devices needed from storage; obtaining a temperature probe from storage; opening the package of the microwave tissue ablation device; inserting the manifold into the console; connecting the saline/water source to a manifold connector; locking a cartridge to the console, etc.

The method 1000 includes a step 1015 initiating the console and the microwave tissue ablation device.

The step of 1015 may further include confirming the pump being working; confirming the temperature of the water/saline being operable; confirming the coolant being properly circulating within the microwave tissue ablation device; confirming the asymmetric dipole antenna of the microwave tissue ablation device being operable; operating the pump for a period of time such that the pump and the microwave tissue ablation device being primed; inserting a distal portion of the tissue ablation device in water; etc.

The method 1000 includes a step 1020 approaching a target tissue with the microwave tissue ablation device under ultrasonic visual guidance.

The step 1020 may further include initiating an ultrasound imaging system (the ultrasound imaging system can be 2D or 3D); inserting the microwave tissue ablation device into a patient's body under ultrasonic visual guidance; securing the microwave tissue ablation device with fixing devices to prevent undesired device movement within the patient's body; securing the cables and tubes attached to the microwave tissue ablation device to prevent undesired torques; positioning the temperature sensor at a desired location; performing CT scan to verify the locations of the microwave tissue ablation device and the target tissue; and repeat any steps as necessary if the location of the microwave tissue ablation device is not intended.

The method 1000 includes a step 1025 activating the microwave tissue ablation device to emit microwaves to heat up a target tissue.

The step 1025 may further include selecting the parameters for the ablation, wherein the parameters includes organ types, organ size, output power, and/or output time; and conducting the necessary electricity to the microwave tissue ablation device to heat up the target tissue. It is noted the steps listed in method 1000 are not sequential.

While the invention is susceptible to various modifications and alternative forms, specific embodiments thereof are shown by way of example in the drawings. The drawings may not be to scale.

The invention will now be described further by way of the following non limiting examples with reference to the figures. These are provided for the purpose of illustration only and other examples falling within the scope of the claims will occur to those skilled in the art in light of these.

FIG. 1 is a schematic side view of the distal end of a microwave tissue ablation device 100, hereinafter the "ablation device," according to one embodiment of the disclosure. The device has been simplified for ease of illustration. FIG. 1 illustrates features of the asymmetric antenna.

As shown in FIG. 1, the ablation device 100 includes a co-axial feedline 110. The feedline 110 includes an inner conductor 102. The feedline 110 includes a first insulator 104 disposed concentrically and circumferentially about the inner conductor 102. The inner conductor 102 may be the power line. The feedline 110 includes an outer conductor 106 disposed concentrically about the first insulator 104. The outer conductor 106 may be the ground line. The feedline 110 includes a second insulator 108 disposed concentrically about the outer conductor 106.

The ablation device 100 includes an asymmetric dipole antenna 120. The asymmetric dipole antenna 120 includes a helical arm 118. The distal end of the helical arm 500 forms an electrical connection with the outer conductor 106 of the feedline 110 at a junction point 117. The helical arm 118 extends proximally from the junction point 117 in a series of turns about the feedline. The helical arm 118 forms no other electrical contact with the inner conductor 102 or the outer conductor 106, except the junction point 117.

The helical arm 118 has a length Lha 124. For each complete helical turn, the height measured axially is a pitch, P 122.

The number of helical turns and pitch (P) can affect the output of microwave energy, the shape of the emission field, and the energy absorption spectrum. The judicious selection of each variable in combination can afford an ablation device with advantageous properties for tissue ablation. See above.

The asymmetric dipole antenna 120 further includes a linear arm 119. The linear arm 119 is electrically connected to the inner conductor 102 of the feedline 110, The linear arm 119 extends distally from a distal end of the inner conductor 102. The linear arm 119 further includes a first portion 131 surrounded by a dielectric 135. This dielectric 135 can be an extension of the first insulator 104 disposed between the inner 102 and outer 106 conductor of the feedline 110. The liner arm 119 further includes a second portion 133 lacking dielectric. The second portion 133 is distal to the first portion 131.

The linear arm 119 has a length Lla 126. The first portion 131 of the linear arm 119 has a length L1 127. The second portion 133 of the linear arm 119 has a length L2 128.

The linear arm does not contact the base 134 of the applicator cap 130.

The antenna and feed line are contained within a shaft 114 having a separate distal applicator cap 130, attached and sealed to the shaft 114. The applicator cap 130 is made of a biocompatible metal or a ceramic, e.g., preferably stainless steel or a ceramic. The portion of the applicator cap 130 distal to the circular base 134 is in a cone shape. The applicator cap 130 includes a sharp end 132 disposed at a distal end of the applicator cap 130 and configured for penetration of tissue. The applicator cap 130 includes a circular base 134 configured to be sealed with the sheath 114.

The ablation device 100 may comprise a cooling system configured to cool the antenna and/or the feed line. FIG. 1A to FIG. 1D provide illustrative embodiments of the device, incorporating cooling systems.

Figure 1A:
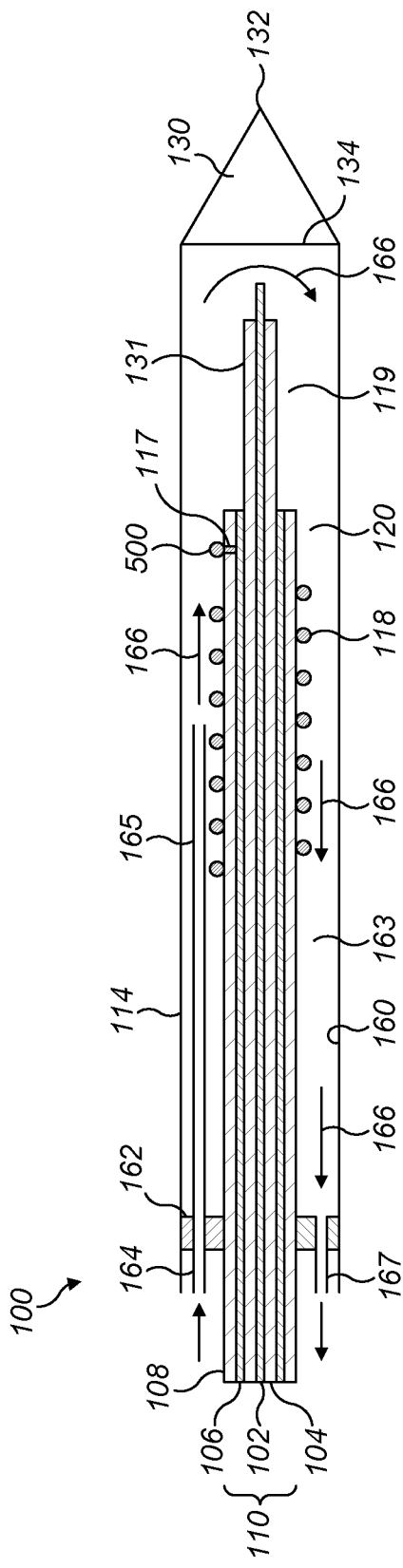
FIG. 1A is a simplified sectional view of a microwave tissue ablation device having a cooling system according to one embodiment of the disclosure.

FIG. 1A illustrates an embodiment a device of the invention having a cooling system. Other features of the device in FIG. 1A are illustrative. As per the device illustrated in FIG. 1, the device illustrated in FIG. 1A 100, includes a co-axial feedline 110 including an inner conductor 102, a first insulator 104 disposed concentrically about the inner conductor 102, an outer conductor 106 disposed concentrically about the first insulator 104 and a second insulator 108 disposed concentrically about the outer conductor 106.

The ablation device 100 also includes an antenna 120 having a helical arm 118, the distal end of which 500 forms an electrical connection with the outer conductor 106 of the feedline 110 at a junction point 117 towards the distal-most end of the feedline. The helical arm 118 extends proximally from the junction point 117 in a series of turns about the feedline 110. The antenna 120 also includes a linear arm 119. The linear arm 119 is electrically connected to the inner conductor 102 of the feedline 110. The linear arm 119 extends distally from a distal end of the inner conductor 102 and includes a first portion 131 surrounded by a dielectric 135, and a second portion 133 lacking dielectric. As in FIG. 1 the linear arm does not touch the applicator cap 130.

The antenna and feed line are contained within a shaft (shown simplified in this FIG. 114 terminating distally in a separate metallic applicator cap 130 having a sharp end 132 disposed at its distal end as per the device of FIG. 1.

A coolant chamber 163 is defined between the inner walls 160 of the shaft 114. The cooling chamber 163 is bounded distally by the base 134 of the cap 130 and proximally by a seal 162 positioned at a point distal of the hub (not shown) and the antenna 120, through which the feedline 110 passes. A coolant inlet conduit 164 and a coolant outlet conduit 167 also pass through the seal 162. The coolant inlet conduit 164 is in the form of a coolant inlet tube 167 disposed within the coolant chamber 163 and displaced radially outward of the feedline 110. The coolant tube is sized and configured to pass between the antenna 120 and the inner wall 160 of the shaft and to deliver coolant from a coolant outlet 165 to a position adjacent a portion of the antenna 120.

The coolant inlet conduit may terminate close to the seal 162 or may be extended so as to deliver cooling fluid to any part of the chamber. Delivery close to the antenna 165 is advantageous because it ensures fresh cooling fluid passes over the antenna. A coolant return tube 167 receives coolant flowing out of the coolant chamber 163. By passing cooling fluid through the cooling chamber in this way, at least a portion of the heat generated in the antenna and/or the feedline can be dissipated.

Figure 1B:
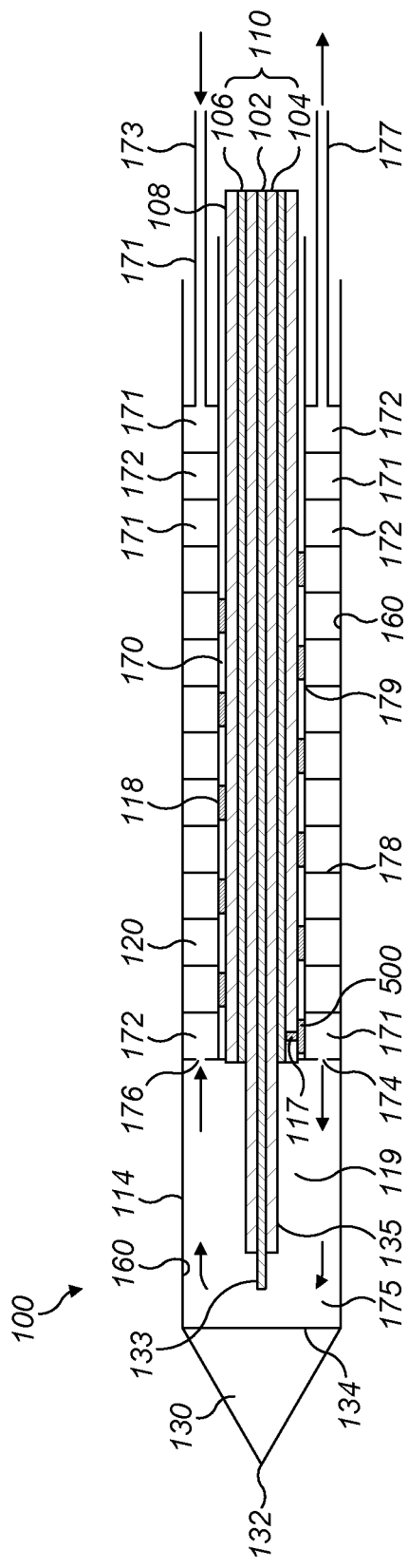
FIG. 1B is a simplified sectional view of a microwave tissue ablation device having an alternative cooling system according to one embodiment of the disclosure.

FIG. 1B illustrates a further embodiment of an ablation device according to the invention. The device illustrated in FIG. 1B 100, includes a co-axial feedline 110 with components as described for FIG. 1A.

The device also includes an asymmetric dipole antenna 120 having a helical arm 118, formed, in this case, of a metallic ribbon as described herein, the distal end of which 500 forms an electrical connection with the outer conductor 106 of the feedline 110 at a junction point 117. The helical arm 118 extends proximally from the junction point 117 in a series of coils about the feedline 110. The ribbon of the helical arm is embedded in an adhesive matrix 170 that binds the ribbon to the outer insulator 108 of the feedline and protects it from damage during manufacture. The antenna 120 also includes a linear arm 119. The linear arm 119 is electrically connected to the inner conductor 102 of the feedline 110. The linear arm 119 extends distally from a distal end of the inner conductor 102 and includes a first portion 131 surrounded by a dielectric 135, and a second portion 133 lacking dielectric. As in FIG. 1 the linear arm is spaced from the base 134 of the applicator cap 130.

As per the antenna of FIG. 1, the antenna and feed line are contained within a shaft (shown simplified in this figure) terminating distally in a pointed metallic or ceramic applicator cap, configured for tissue penetration.

A cooling system is provided which is configured to circulate coolant over the antenna and at least a part of the feedline, The cooling system comprises a pair of cooling conduits 171, 172, each arranged about, and coaxial with, a portion of the feedline and the helical portion of the antenna. Each conduit is in the form of a helix the two conduits being interdigitated one with the other to form a double helix. Coolant is delivered to the inlet of the first conduit, 171, by the coolant inlet tube 173. It passes through the first cooling conduit 171, passes over the antenna and feedline, and exits at the outlet orifice 174 into a coolant mixing chamber 175, that bathes the remainder of the antenna (in this case the linear arm), as far as the antenna cap base 134. Coolant then enters the coolant return conduit 172 via the coolant return orifice 176, passes through the coolant return conduit and returns via the coolant return conduit 172 and passes to the coolant return pipe 177. The helical cooling conduits 171, 172 are separated by proximal and distal walls 178, 900 formed as a pair of helical dividing ribbons extending perpendicularly from the inner surface 160 of the shaft 114 and extending distally in a double helix so as to form the two helical conduits 171, 172 between them. The inner most extremity of the dividing ribbon 179 sealing against the matrix 170 around the ribbon of the antenna to form the two helical conduits.

FIG. 1C illustrates a further embodiment of an ablation device according to the invention. The device illustrated in FIG. 1C 100, includes a co-axial feedline 110 with components as described for FIG. 1A.

The device includes an asymmetric dipole antenna 120 having a helical arm 118, formed, of a metallic ribbon attached to the outer insulator 108 for example by an adhesive (not shown). The distal end of the helical portion 500 forms an electrical connection with the outer conductor 106 of the feedline 110 at a junction point 117. The helical arm 118 extends proximally from the junction point 117 in a series of helical turns about the feedline 110.

The antenna 120 also includes a linear arm 119. The linear arm 119 is electrically connected to the inner conductor 102 of the feedline 110. The linear arm 119 extends distally from a distal end of the inner conductor 102 and includes a first portion 131 surrounded by a dielectric 135, and a second portion 133 lacking dielectric. The linear arm does not touch the applicator cap 130.

A cooling chamber 163 surrounds the feedline 183 and the antenna 120. The cooling chamber is defined between the inner wall 160 of the shaft 114, and the antenna 120 and feedline 183 and the base 134 of the applicator cap 130. The device comprises a cooling tube 182, co-axial with the feedline 110 and antenna 120 and extending distally to a point towards the end of the linear arm of the antenna 184. The cooling tube 182 divides the cooling chamber 163 into a first cooling conduit 180, co-axial with a distal portion of the feedline 183 and extending over the helical portion 118 and the linear portion 119 of the antenna 120; and a second cooling conduit co-axial with the first extending between the outer wall of the cooling tube 182 and the inner wall 160 of the sheath 114. The cooling tube 182 and the first and second conduits are open at the distal end allowing the cooling fluid to circulate through a cooling fluid mixing chamber 185 between the base 134 of the applicator cap 130 and the distal end of the cooling tube 182. The first and second cooling conduits co-operate to provide coolant circulation over the antenna. The first cooling conduit may be the coolant inflow and the second the coolant outflow or vice versa. This arrangement of cooling conduits allows the antenna to be cooled to the tip.

FIG. 1D illustrates a yet further embodiment of an ablation device according to the invention. The device illustrated in FIG. 11) 100, includes a co-axial feedline 110 including an inner conductor 102, a first insulator 104 disposed concentrically about the inner conductor 102, an outer conductor 106 disposed concentrically about the first insulator 104. The feedline illustrated has no outer insulation and is in contact with the cooling fluid in use.

The device includes an asymmetric dipole antenna 120 having a helical arm 118, formed, in this example of a wire, but which may also be in ribbon form. The antenna 120 also includes a linear arm 119, The linear arm 119 is electrically connected to the inner conductor 102 of the feedline 110. The linear arm 119 extends distally from a distal end of the inner conductor of the feedline 102 and includes a first portion 131 surrounded by a dielectric 135, and a second portion 133 lacking dielectric. As in FIG. 1 the linear arm does not touch the applicator cap 130.

A cooling chamber 163 is defined between the inner face 160 of the shaft 144 and the base 134 of the applicator cap 130 and surrounds the antenna 120. The distal portion of the feedline and the antenna lie within the cooling chamber 163. The device comprises a cooling tube 182, co-axial with the feedline 110 and extending distally to a point towards the distal end 184 of the linear arm 119 of the antenna. The cooling tube 182 divides the cooling chamber 163 into a first cooling conduit 180, co-axial with a distal portion of the feedline 183 and extending over the linear portion 119 of the antenna 120; and a second cooling conduit 181 co-axial with the first and extending between the outer wall of the cooling tube 182 and the inner wall 160 of the shaft 114. The cooling tube 182 and the first and second conduits are open at the distal end allowing the cooling fluid to circulate through a cooling fluid mixing chamber 185 between the base 134 of the applicator cap 130 and the distal end 186 of the cooling tube 182.

The helical arm 118 of the antenna 120 is wound about the outer surface of the coolant tube. The distal end 500 of the helical arm 118 forms an electrical connection with the outer conductor 106 of the feedline 110 at a junction point 117. The helical arm 118 extends proximally from the junction point 117 in a series of helical coils about the feedline 110 on the surface of the cooling tube. The first and second cooling conduits co-operate to provide coolant circulation over the antenna. The first cooling conduit may be the coolant inflow and the second the coolant outflow or vice versa. This allows the antenna to be cooled to the tip.

FIG. 2 shows a schematic view of the distal portion of a microwave tissue ablation device and illustrates four embodiments of the metal cap and the relationship between the distal end of the antenna and the cap 202.

FIG. 2A shows a schematic view of a microwave tissue ablation device 200 with a metal cap 202 according to one embodiment of the invention. The metal cap 202 is conical and has a circular base 203. A solid-cylinder protrusion 204 subtends from the base 203 and has base 214, the cap has a shoulder 205 allowing the cap 202 to be inserted into the distal end of the device shaft 206 which may be metallic or ceramic. The cap may be fixed to the shaft by an adhesive (not shown). The microwave tissue ablation device 200 further includes an asymmetric dipole antenna 207 shown in simple form here and discussed in detail elsewhere herein. The antenna comprises a helical arm 211 and a linear arm 208. The linear arm having a proximal portion 209 surrounded by a dielectric 212 and a free distal portion 210 having no dielectric. The distal portion of the linear arm 210 has a tip 213 which is separated from the cap by a distance $H_g$. Adjusting the distance between the tip 213 and the cap alters the degree to which the metallic cap is electromagnetically coupled to the antenna, which changes the shape of the energy emission field and hence the shape of the ablation zone (see also FIG. 8).

FIG. 2B illustrates a further embodiment. The microwave tissue ablation device 225 includes a metal cap which is conical and has a circular base 226. The metal cap 225 includes a base 227 from which subtends a hollow-cylinder protrusion 228. The cap has a shoulder 231 allowing the cap 226 to be inserted into the distal end of the device shaft 232. The cap may be fixed to the shaft by an adhesive (not shown). The microwave tissue ablation device 225 further includes an asymmetric dipole antenna 229 with features as described in FIG. 2A.

As shown in FIG. 2B, a gap $H_G$ 229 is disposed between the proximal end of the hollow-cylinder protrusion 228 and the distal end of the asymmetrical dipole antenna 230.

FIG. 2C is a schematic view of a microwave tissue ablation device 235 with a metal cap 236 according to one embodiment of the invention. The metal cap 236 is a circular based cone having a base 237. The microwave tissue ablation device 225 further includes an asymmetric dipole antenna 239 with features as described in FIG. 2A.

The metallic cap 236 is affixed directly to the distal end 240 of the device shaft 241. The distal tip of the linear arm of the antenna 239 is a distance Hg 238 away from the base of the cap 236. The gap $H_G$ 238 is axially disposed between the proximal end of base 237 and the distal end of the asymmetric dipole antenna 239.

FIG. 2D is a schematic view of a microwave tissue ablation device 245 with a metal cap 246 according to one embodiment of the invention. The metal cap 277 is conical and has a circular base 248. A cylindrical protrusion 249 subtends from center of the circular base 247 leaving a shoulder 248 which allows the cylindrical protrusion to be inserted into the distal end of the device shaft 255. A blind ending cylindrical void or pocket 250 is formed centrally on the base of the cylindrical protrusion and is configured to accept a length Hp 259 of the distal portion 252 of the linear arm of the antenna which is axially and radially spaced from the walls 258 of the void 250.

Other features of the antenna are as described in FIG. 2A.

Figure 3:
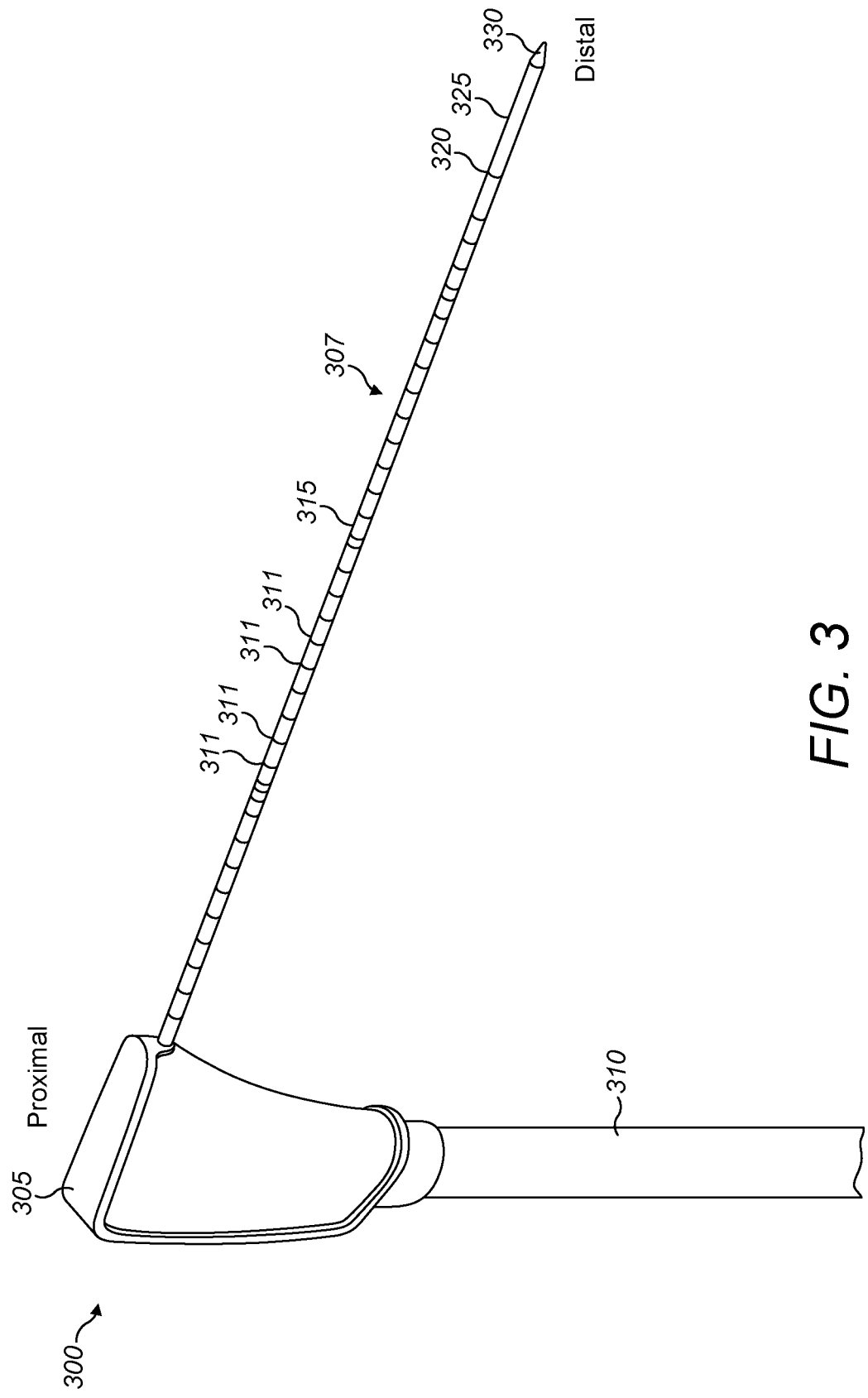
FIG. 3 is a perspective view of a microwave tissue ablation device with its handle according to one embodiment of the disclosure.

FIG. 3 is a perspective view of a microwave tissue ablation device 300 with a handle 305 according to one embodiment of the disclosure.

The microwave tissue ablation device 300 includes a handle 305. The handle 305 is configured to provide a firmer grip for a surgeon to handle the tissue ablation device 300. The handle is further configured to house liquid manifolds for coolant circulation and co-axial connectors for powering the feedline.

The microwave tissue ablation device 300 includes a probe 307. The probe 307 is configured to be inserted into patient's body for heating up the target tissue. In one embodiment, the probe 307 includes all the components of the ablation device 100 as shown in FIGS. 1, and 1A to 1D, such as the feedline, asymmetric dipole antenna, coolant system having inflow tubes and coolant outflow tubes, etc.

The probe 307 includes a surface 315. The surface 315 is configured to be in contact with human tissue and is made with biocompatible materials. The device shaft 315 is at least partially, metal, e.g., stainless steel and includes markings 311, e.g., laser markings. The markings 311 are configured to inform the surgeon of the depth of the probe penetration into the body. It may comprise a lubricious surface layer such as PTFE, to aid insertion and prevent tissue sticking to it.

The probe 307 further includes a trocar tip 330. In one embodiment, the trocar tip 330 can be the applicator cap 130 shown in FIGS. 1 to 1D, FIG. 2A-D or FIG. 4 for example.

The probe 307 further includes an echogenic region 325 that extends at least to cover the region of the probe about the antenna. The echogenic region 325 is configured to be visible under ultrasound, imaging and one embodiment, comprises a coating comprising acoustically-reflective microspheres.

The probe 307 further includes a region 320 configured to relieve strain on the probe induced during use, such as that caused by flexing of the shaft. This strain relief region is particularly useful when the distal portion of the probe sheath is ceramic as described above The strain relief area 320 is configured to provide the probe 307 added flexibility avoiding fracture of the probe 307 during medical operation.

The microwave tissue ablation device 300 includes a housing 310. The housing 310 houses coaxial cables, fluid lines, electric lines, etc.

Figure 4A:
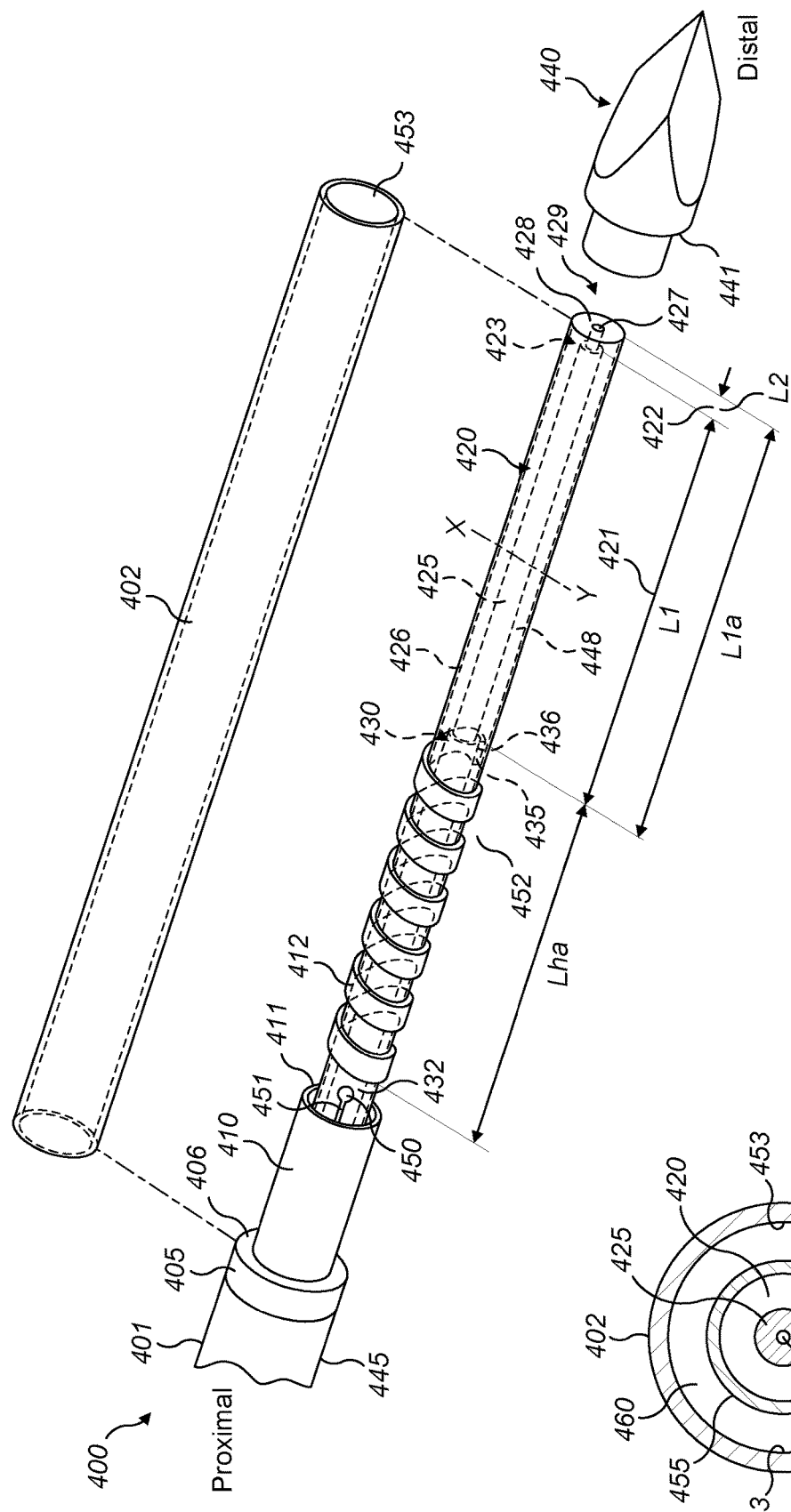
FIG. 4A is a perspective view of a microwave tissue ablation device according to one embodiment of the disclosure.
Figure 4B:
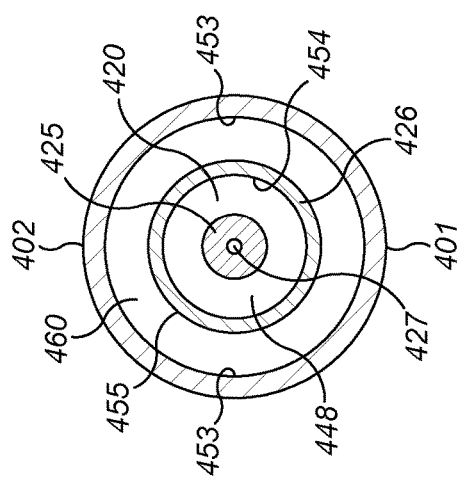
FIG. 4B is a sectional schematic view of a microwave tissue ablation device according to one embodiment of the disclosure. The section is taken through X-Y of FIG. 4A.

FIG. 4A is a perspective view of a microwave tissue ablation device 400 according to one embodiment of the disclosure. FIG. 4B is a sectional view across the line XY to illustrate one embodiment of the cooling features.

The tissue ablation device has a shaft 401 having a metal portion 445 and a ceramic portion 402. The ceramic portion extending from distal end 406 of the collar 405 to the base 441 of the cap 440. The ceramic portion is shown displaced, in order to show the internal features of the device.

The tissue ablation device 400 includes a resilient element 405, and an adaptor 410 to joint the metal shaft 445 to the ceramic portion of the shaft 402. In devices of the invention, the adaptor takes up any difference in shaft thickness between the two portions and additionally acts to reduce flexing between the metal shaft 445 and the ceramic portion. In devices of the invention, the resilient annular spacer between the ceramic portion and the metal portion of the shaft as shown here, acts to provide resilience to this region and so reduce the occurrence of fractures at this point due to strain on the shaft during use.

The tissue ablation device 400 may include a temperature sensor 450 housed next to the internal adaptor 410 and having an electrical connection 451 via the hub to the control unit.

The tissue ablation device 400 has an antenna 452 including a helical arm 412, and a linear arm 420. A distal end 435 of the helical arm 412 forms an electrical connection with the outer conductor 430 of the feedline 432 at a junction point 436. The helical arm 412 extends proximally from the junction point 436 in a series of turns about the feedline 432. The helical arm 412 forms no other electrical contact with the inner conductor 427 or the outer conductor 430, except the junction point 436. The helical arm is coiled on a tube 426, which extends from the hub (not shown), through the metal portion of the shaft 445 to the tip of the antenna 428. The electrical connection between the helical arm 412 of the antenna and the outer conductor of the feedline 432 passes through the tube at the junction point 436. The helical arm 412 has a length (Lha) whose dimensions are discussed elsewhere herein.

The tube 426 defines a first cooling conduit 448 between the inner wall 454 of the tube 426 and the feedline 432 and a second cooling conduit 460 between the outer wall 455 of the tube 426 and the inner wall of the shaft 453. Cooling fluid may be pumped through the space between the tube 426 and the feedline 432 to a mixing chamber 429 between the tube 426 and the cap 440 and returns in the space between the outside of the tube 426 and the ceramic portion of the shaft, through the space 411 between the inside of shaft and the adaptor 410 and back down the shaft 445 to the hub.

The linear arm 420 is an extension of the inner conductor 427 of the feedline 432 and is surrounded by a dielectric layer 425, except for the distal portion 423, which is free of dielectric.

The linear arm 420 of the asymmetric dipole antenna has a length Lla. The linear arm includes a first portion L1 421 coated with an insulator, which is an extension of the first dielectric layer of the feedline 432 which is disposed between the inner conductor 427 and the outer conductor 430 and is not visible in this view.

The linear arm 420 further includes a second portion 423 which has a length L2 422 and which is not coated with the insulator. In one embodiment, the second portion L2 422 is exposed to the circulating coolant.

The device 400 includes a trocar tip 440. In one embodiment, the trocar tip 440 can be the applicator cap 130 shown in FIG. 1, the metal caps shown in FIGS. 2A-2D, and the trocar tip 330 shown in FIG. 3. The trocar tip 440 can be made with stainless steel and/or ceramic.

Figure 5:
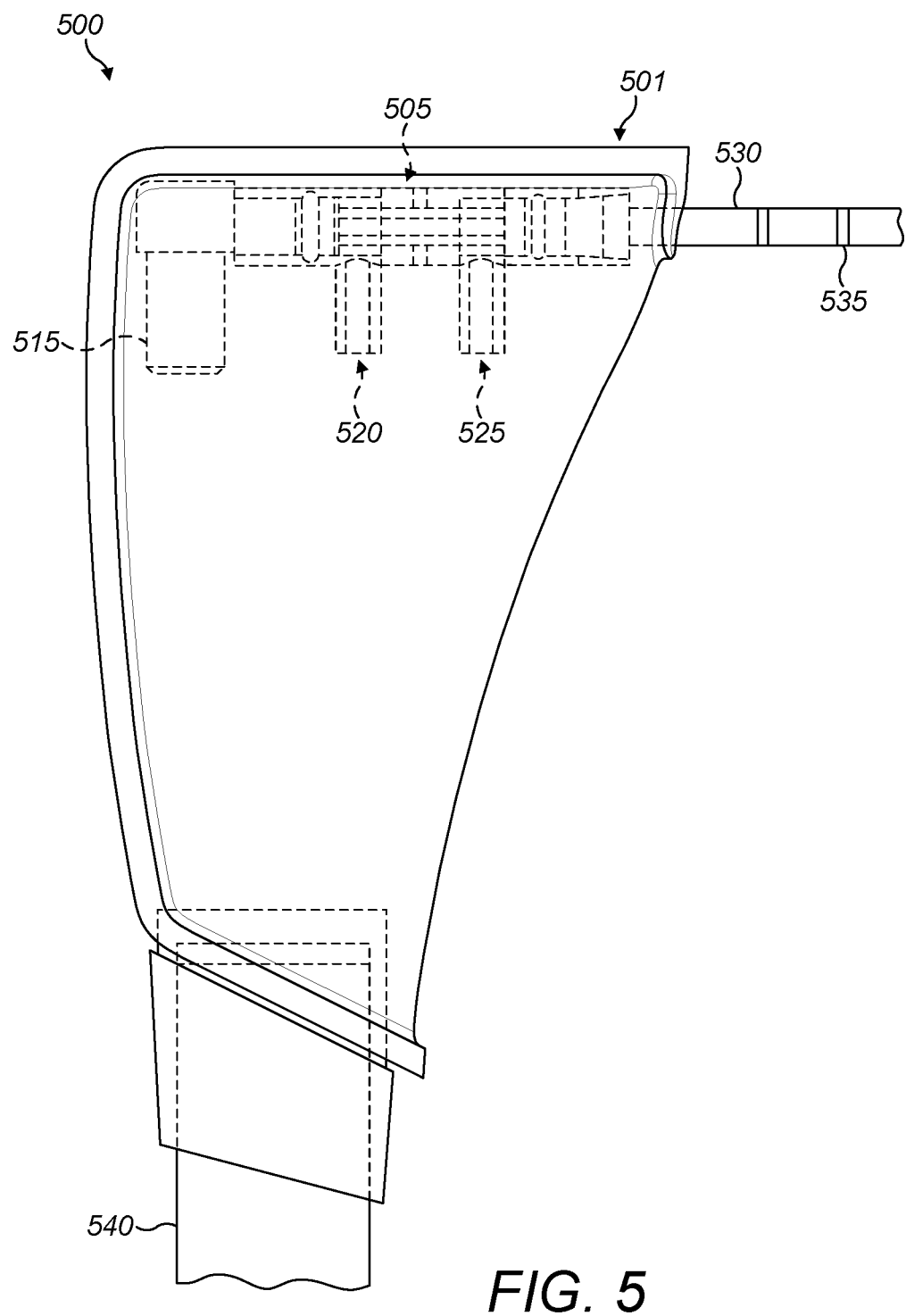
FIG. 5 is a side view of the handle of the microwave tissue ablation device according to one embodiment of the disclosure.

FIG. 5 is a side view of a microwave tissue ablation device of the invention 500. The ablation device 500 includes a handle 501. The handle 501 houses a manifold 505.

The manifold 505 electrically connects the power source (not shown) and the tissue ablation probe 530 through the coaxial cable connector 515. The tissue ablation probe 530 includes markings 535 configured to inform surgeons of the depth of probe penetration during surgery.

The manifold 505 also fluidically connects the coolant source (not shown) and the tissue ablation probe 530. The manifold 505 includes a coolant inlet 520 and a coolant outlet 525. The coolant inlet 520 is fluidically connected to the coolant inflow conduit and the coolant outlet 525 is fluidically connected to the coolant outflow conduit.

The tissue ablation device 500 further includes tubular housing 540 that houses the electric wires and fluid tubes.

Figure 6A:
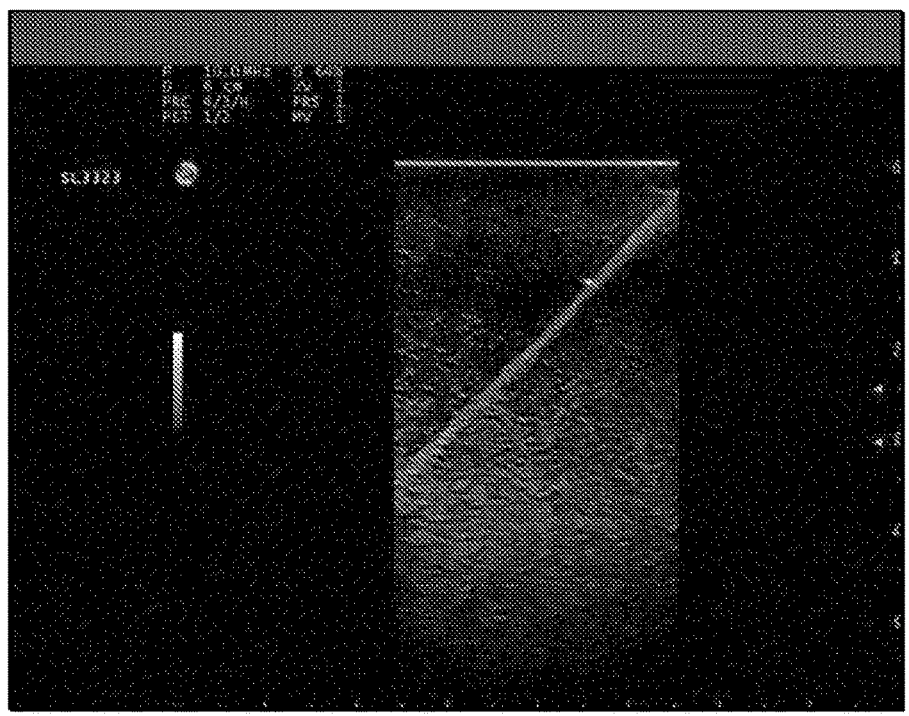
FIG. 6A shows an ultrasound image of the tissue ablation probe without echogenic coating according to one embodiment of the disclosure.
Figure 6B:
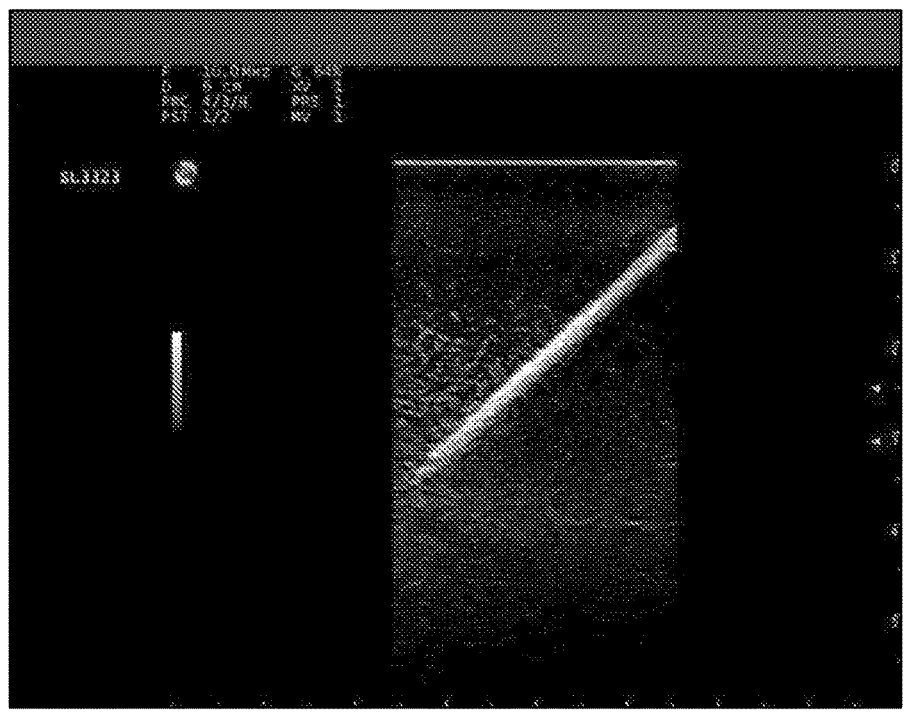
FIG. 6B shows an ultrasound image of the tissue ablation probe with echogenic coating according to one embodiment of the disclosure.

FIGS. 6A and 6B compare ultrasound images of the tissue ablation probe without echogenic coating (6A) and with echogenic coating. FIG. 6B. The echogenic coating provides additional assistance in accurately placing the tissue ablation probe in the patient's tissue.

Figure 7A:
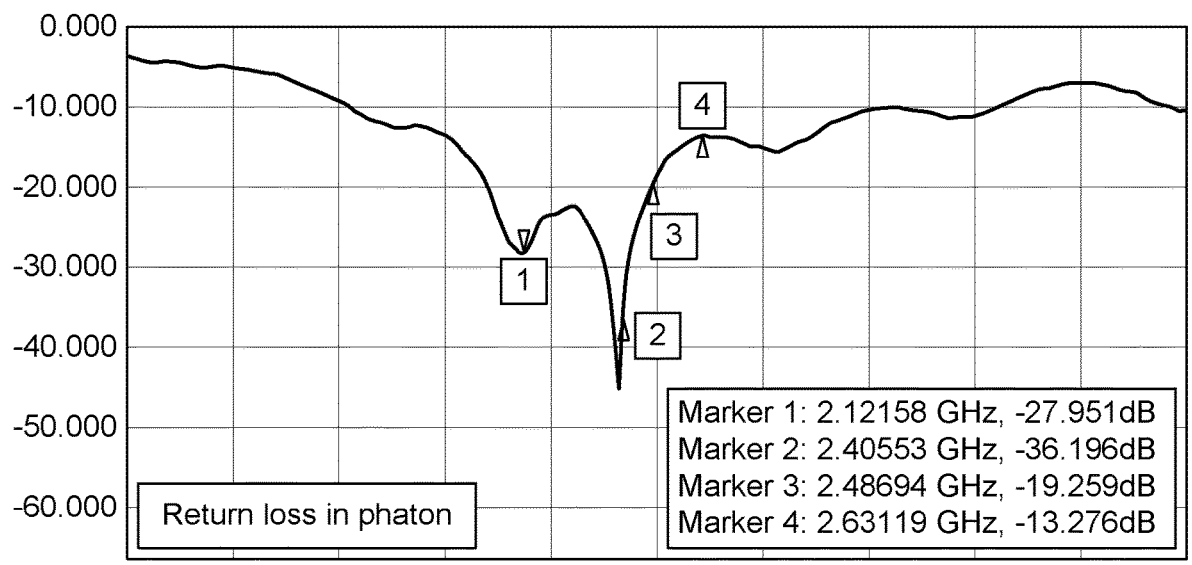
FIG. 7A is an energy absorption frequency spectrum of a tissue ablation probe according to one embodiment of the disclosure.

FIG. 7A is an energy absorption frequency spectrum of a tissue ablation probe according to one embodiment of the disclosure. The x-axis of FIG. 7A is frequency (GHz). The y-axis of FIG. 7A is energy absorption (dB). FIG. 7A shows the energy absorption under different microwave frequencies. Marker 1 in FIG. 7A shows the microwave frequency of 2.12158 GHz; the energy absorption by the surrounding tissue is −27.951 dB. Marker 2 in FIG. 7A shows the microwave frequency of 2.40553 GHz; the energy absorption by the surrounding tissue is −27.951 dB. Marker 3 in FIG. 7A shows the microwave frequency of 2.48694 GHz; the energy absorption by the surrounding tissue is −27.951 dB. Marker 4 in FIG. 7A shows the microwave frequency of 2.63119 GHz; the energy absorption by the surrounding tissue is −13.276 dB.

Figure 7B:
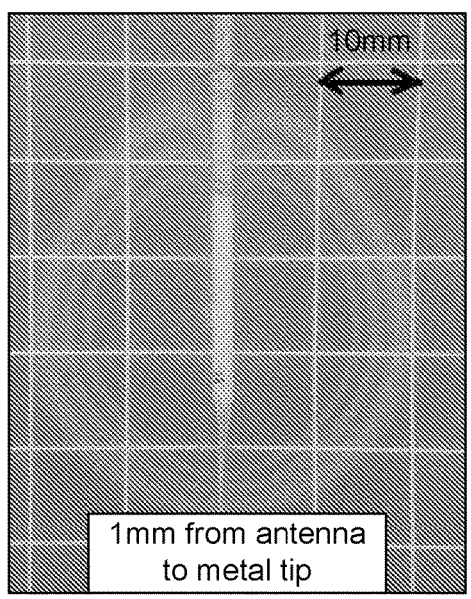
FIG. 7B is a picture showing the energy emission field of a tissue ablation probe according to one embodiment of the disclosure.

FIG. 7B is a picture showing the energy emission field of a tissue ablation probe according to one embodiment of the disclosure. The ablation device tested in FIG. 7B has an asymmetric dipole antenna with 1 mm gap between the distal end of the linear arm of the tissue ablation device and the proximal end of the metal cap. The dividing squares shown in FIG. 7B is 10 mm×10 mm.

Figure 7C:
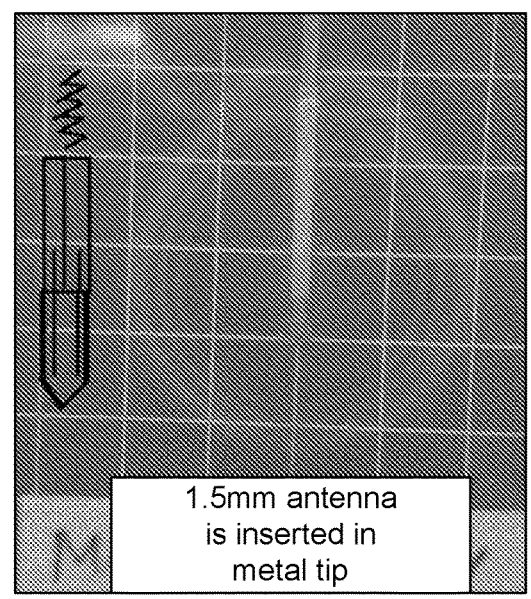
FIG. 7C is a picture showing the energy emission field of a tissue ablation probe according to one embodiment of the disclosure.

FIG. 7C is a picture showing the energy emission field of a tissue ablation probe according to one embodiment of the disclosure. The ablation device tested in FIG. 7C has 1.5 mm axially overlapping distance between a distal portion of the linear arm of an asymmetric dipole antenna with and a proximal portion of the metal cap. The dividing squares shown in FIG. 7C is 10 mm×10 mm.

Figure 8C:
FIG. 8C is a picture showing the ablation pattern produced in bovine liver of an of a tissue ablation probe according to one embodiment of the disclosure.
Figure 8B:
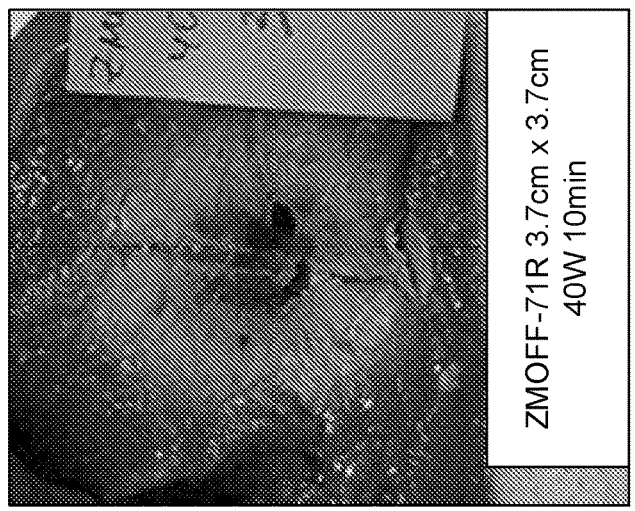
FIG. 8B is a picture showing the ablation pattern produced in bovine liver of an of a tissue ablation probe according to one embodiment of the disclosure.
Figure 8A:
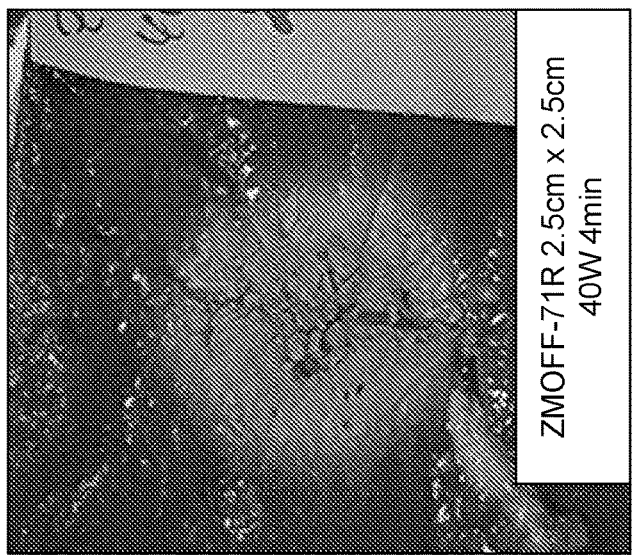
FIG. 8A is a picture showing the ablation pattern produced in bovine liver of an ablation probe according to one embodiment of the disclosure.

FIG. 8A is a picture showing ablation effect of a tissue ablation probe using bovine liver according to one embodiment of the disclosure. The animal tissue was heated for 40 W over 4 mins. The ablation size is 2.5 cm×2.5 cm.

FIG. 8B is a picture showing ablation effect of a tissue ablation probe using bovine liver according to one embodiment of the disclosure. The animal tissue was heated for 40 W over 10 mins. The ablation size is 3.7 cm×3.7 cm.

FIG. 8C is a picture showing ablation effect of a tissue ablation probe using bovine liver according to one embodiment of the disclosure. The animal tissue was heated for 100 W over 10 mins. The ablation size is 5.0 cm×5.2 cm.

Figure 9:
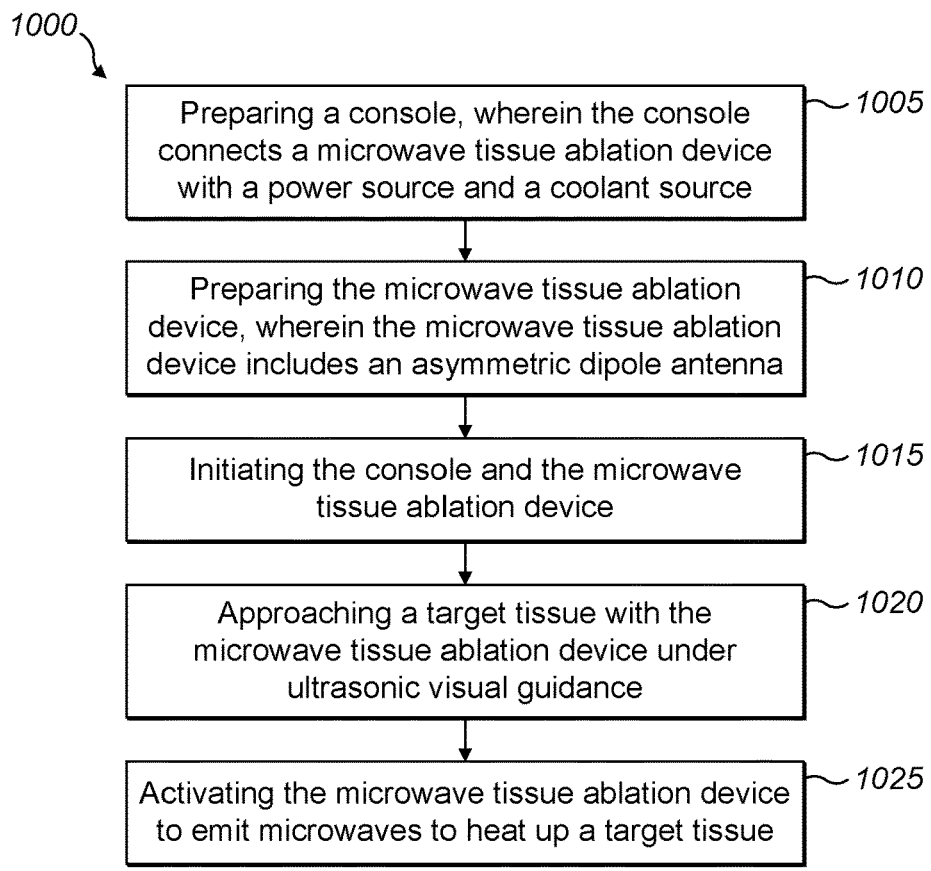
FIG. 9 is a method of using a microwave ablation device according to one embodiment of the disclosure.

FIG. 9 is a method 1000 of using a microwave ablation device according to one embodiment of the disclosure.

The method 1000 includes a step 1005 preparing a console, wherein the console connects a microwave tissue ablation device with a power source and coolant source. In one embodiment, the console may support more than one microwave tissue ablation devices. For example, one console may support three or four tissue ablation devices providing sufficient electricity and coolant supply to each of the tissue ablation devices.

The method 1000 includes a step 1010 preparing the microwave tissue ablation device, wherein the microwave tissue ablation device includes an asymmetric dipole antenna. The microwave tissue ablation device in method 1000 can be the microwave tissue ablation devices shown in FIGS. 1-7.

The step 1010 may further include gathering other necessary supplies; obtaining room temperature sterile saline/water; obtaining an intravenous pole; placing the intravenous pole close to the surgery table; identifying target tissue location; determining a number of microwave tissue ablation device needed; obtaining the microwave tissue ablation devices needed from storage; obtaining a temperature probe from storage; opening the package of the microwave tissue ablation device; inserting the manifold into the console; connecting the saline/water source to a manifold connector; locking a cartridge to the console, etc.

The method 1000 includes a step 1015 initiating the console and the microwave tissue ablation device.

The step of 1015 may further include confirming the pump being working; confirming the temperature of the water/saline being operable; confirming the coolant being properly circulating within the microwave tissue ablation device; confirming the asymmetric dipole antenna of the microwave tissue ablation device being operable; operating the pump for a period of time such that the pump and the microwave tissue ablation device being primed; inserting a distal portion of the tissue ablation device in water; etc.

The method 1000 includes a step 1020 approaching a target tissue with the microwave tissue ablation device under ultrasonic visual guidance.

The step 1020 may further include initiating an ultrasound imaging system (the ultrasound imaging system can be 2D or 3D); inserting the microwave tissue ablation device into a patient's body under ultrasonic visual guidance; securing the microwave tissue ablation device with fixing devices to prevent undesired device movement within the patient's body; securing the cables and tubes attached to the microwave tissue ablation device to prevent undesired torques; positioning the temperature sensor at a desired location; performing CT scan to verify the locations of the microwave tissue ablation device and the target tissue; and repeat any steps as necessary if the location of the microwave tissue ablation device is not intended.

The method 1000 includes a step 1025 activating the microwave tissue ablation device to emit microwaves to heat up a target tissue.

The step 1025 may further include selecting the parameters for the ablation, wherein the parameters includes organ types, organ size, output power, and/or output time; and conducting the necessary electricity to the microwave tissue ablation device to heat up the target tissue. It is noted the steps listed in method 1000 are not sequential.

Figure 10:
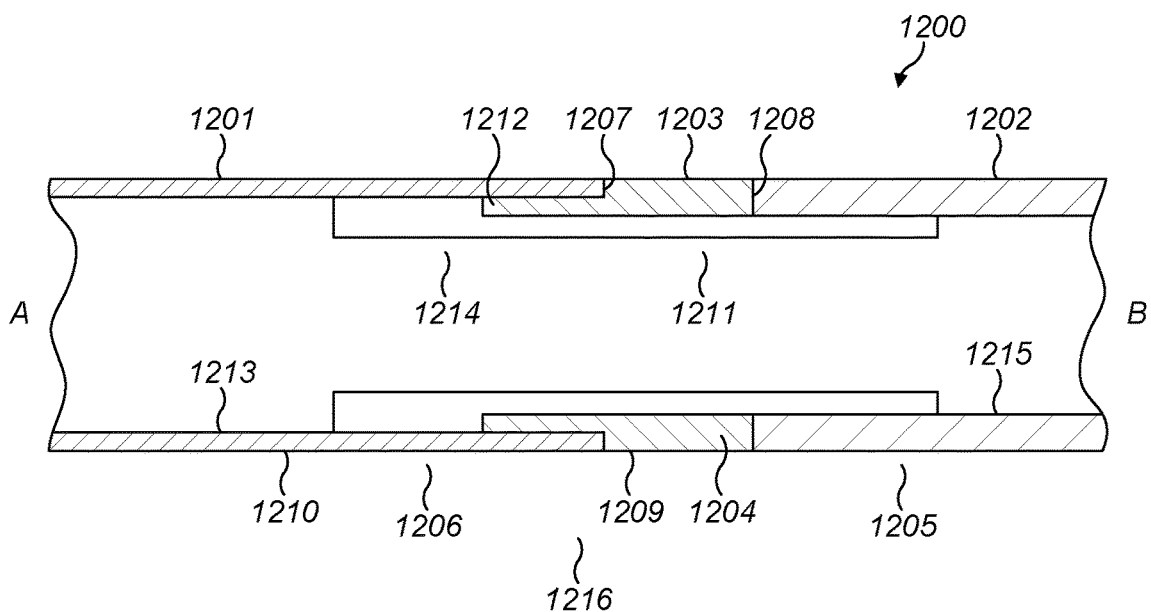
FIG. 10 is a enlarged view of a section of an ablation device shaft showing a joint between a metallic portion and a ceramic portion of the shaft.

FIG. 10 shows a section through one embodiment of a device shaft 1200. The proximal end is indicated by A and the distal end by B. Other features such as the coaxial cable, antenna and cooling system are omitted for clarity. The shaft has a proximal metallic portion 1201, and a distal non metallic portion, which is preferably made of ceramic 1202. The shaft comprises a strain relief region 1216, comprising a resilient element 1203, positioned between the metallic and non metallic portions of the shaft, and an adapter sleeve 1214, radially inward of the resilient element 1203.

The resilient element comprises a resilient annular spacer 1204, shaped and configured to space apart the proximal end of the non metallic portion 1205, from the distal end of the metallic portion 1206. The spacer is configured to abut the metallic portion on a proximal face 1207 and the non metallic portion on a distal face 1208. The spacer extends radially outward to form a surface 1209, that is flush with the outer surface of the probe shaft 1210. The radially innermost portion of the annular spacer, 1211 extends proximally to provide an annular step 1212, configured to support the inner face of the distal end of the metallic portion 1213. An adaptor sleeve 1214, extends each side of the joint between the metallic and non metallic sections and radially inward of the annular spacer 1203. Preferably the sleeve extends proximally of the annular spacer 1203, and is configured to be in contact with and support the inner face of the distal end of the metallic portion of the shaft 1213. The sleeve extends distally of the spacer 1203, and is configured to be in contact with and support the inner face of the proximal end of the ceramic portion of the shaft 1215.

While the invention is susceptible to various modifications and alternative forms, some specific embodiments thereof are shown by way of example in the drawings. The drawings may not be to scale.

The invention claimed is:

1. A microwave ablation probe comprising
    a feedline having an inner conductor, an outer conductor and a dielectric disposed there- between; and
    an antenna, the antenna including,
        a helical arm, a distal end of the helical arm being electrically connected to the outer conductor of the feedline at a junction point, the helical arm co-axially disposed about the feedline and extending in a proximal direction from the junction; and
        a linear arm, the linear arm being electrically connected to the inner conductor of the feedline, the linear arm extending distally from a distal end of the feedline, the linear arm further including
            a first portion surrounded by a dielectric, and
            a second portion free of dielectric, the second portion being distal to the first portion;
    wherein the linear arm is the distal most portion of the antenna.

2. A microwave ablation probe according to claim 1, comprising a shaft, the antenna and feedline disposed within the shaft.

3. A microwave ablation probe according to claim 2, wherein the shaft comprises a metal portion and a ceramic portion, the ceramic portion extending axially to be at least coextensive with the antenna.

4. A microwave ablation probe according to claim 1, comprising a cooling system configured to pass a coolant fluid over the antenna.

5. A microwave ablation probe according to claim 4, wherein the cooling system is configured to pass a coolant fluid over at least a portion of the feedline and over the antenna.

6. A microwave ablation probe according to claim 4, wherein the cooling system comprises a coolant chamber defined between the inner walls of the device shaft.

7. A microwave ablation probe according to claim 6, wherein the cooling system comprises a cooling tube disposed about the feedline.

8. A microwave ablation probe according to claim 7, wherein the cooling tube divides the cooling chamber into a first cooling conduit and a second cooling conduit, the first cooling conduit disposed between the feedline and the inner wall of the cooling tube and the second cooling conduit disposed between the outer wall of the cooling tube and the inner wall of the device shaft.

9. A microwave ablation probe according to claim 7, wherein the helical arm of the antenna is wound about the cooling tube and extends proximally from the junction point in a series of turns about the cooling tube.

10. A microwave ablation probe according to claim 7, wherein the helical arm of the antenna is wound about the feedline and extends proximally from the junction point in a series of turns about the feedline.

11. A microwave ablation probe according to claim 1, comprising a metallic cap.

12. A microwave ablation probe according to claim 11, wherein the linear arm of the antenna is electromagnetically coupled to the metallic cap but is not connected to the cap.

13. A microwave ablation probe according to claim 11, wherein the distal tip of the antenna is separated from the cap by a distance of 0.2 mm to 3 mm.

14. A microwave ablation probe according to claim 1 wherein the helical arm does not extend distally to the junction point along the length of the microwave ablation probe.

15. A microwave ablation probe according to claim 1, wherein the linear arm spans a linear arm length, wherein the helical arm spans a helical arm length, and wherein a ratio of the linear arm length to the helical arm length is between 0.75 and 14.

16. A microwave ablation probe according to claim 1, wherein the linear arm length is between 4 mm and 14 mm.

17. A microwave ablation system comprising one or more microwave ablation probes, each microwave ablation probe comprising
    a feedline having an inner conductor, a dielectric coaxially disposed about the inner conductor and an outer conductor coaxially disposed about the dielectric; and
    an antenna, the antenna including,
        a helical arm, a distal end of the helical arm being electrically connected to the outer conductor of the feedline at a junction point, the helical arm coaxially disposed about the feedline and extending in a proximal direction from the junction point; and
        a linear arm, the linear arm being electrically connected to the inner conductor of the feedline, the linear arm extending in a distal direction from a distal end of the feedline, the linear arm further including
            a first portion surrounded by a dielectric, and
            a second portion free of dielectric, the second portion being distal to the first portion;
        wherein the helical arm and the linear arm do not overlap along the length of the microwave ablation probe and wherein the linear arm is the distal most portion of the antenna;
    a power module configured to provide microwave energy to the microwave antenna of the, or each microwave ablation probe and;
    one or more power cables configured to connect the power module to each microwave antenna and to deliver microwave energy provided by the power module to the antenna for the ablation of tissue.

18. A microwave ablation system according to claim 17, wherein each microwave ablation probe comprises a cooling system to cool the antenna and/or at least a portion of the feed line;
    the ablation system additionally comprising a cooling system configured to deliver coolant fluid to the cooling system of the microwave ablation probe, to cool the antenna and at least a portion of the feedline.

19. A microwave ablation system according to claim 17, wherein each power cable is a cooled power cable and the system additionally comprises a cooling system configured to cool the or each power cable.

20. A microwave ablation probe comprising
    a feedline having an inner conductor, an outer conductor and a dielectric disposed there- between; and
    an antenna, the antenna including,
        a helical arm spanning a helical arm length, a distal end of the helical arm being electrically connected to the outer conductor of the feedline at a junction point, the helical arm co-axially disposed about the feedline and extending in a proximal direction from the junction; and a linear arm spanning a linear arm length, the linear arm being electrically connected to the inner conductor of the feedline, the linear arm extending distally from a distal end of the feedline, the linear arm further including a first portion surrounded by a dielectric, and a second portion free of dielectric, the second portion being distal to the first portion;

wherein the helical arm does not extend distally to the junction point along the length of the microwave ablation probe; and wherein a ratio of the linear arm length to the helical arm length is between 0.75 and 14.

* * * * *